United States Patent
Hasan et al.

(10) Patent No.: US 10,874,107 B2
(45) Date of Patent: Dec. 29, 2020

(54) β-LACTAMASE TARGETED PHOTOSENSITIZER FOR PESTICIDE AND PEST DETECTION

(71) Applicants: The General Hospital Corporation, Boston, MA (US); New England Biolabs, Ipswich, MA (US)

(72) Inventors: Tayyaba Hasan, Arlington, MA (US); Ulysses W. Sallum, Arlington, MA (US); Barton Slatko, Ipswich, MA (US); Jeremy Foster, Beverly, MA (US)

(73) Assignees: The General Hospital Corporation, Boston, MA (US); New England Biolabs, Ipswich, MA (US)

( * ) Notice: Subject to any disclaimer, the term of this patent is extended or adjusted under 35 U.S.C. 154(b) by 0 days.

(21) Appl. No.: 16/013,333

(22) Filed: Jun. 20, 2018

(65) Prior Publication Data
US 2020/0154710 A1    May 21, 2020

Related U.S. Application Data

(63) Continuation of application No. 14/410,389, filed as application No. PCT/US2013/047045 on Jun. 21, 2013, now abandoned.

(60) Provisional application No. 61/663,410, filed on Jun. 22, 2012.

(51) Int. Cl.
*A01N 43/90* (2006.01)
*A01N 25/00* (2006.01)
*C07D 501/16* (2006.01)
*G01N 21/64* (2006.01)

(52) U.S. Cl.
CPC ............. *A01N 43/90* (2013.01); *A01N 25/00* (2013.01); *C07D 501/16* (2013.01); *G01N 21/6428* (2013.01); *G01N 2021/6432* (2013.01); *G01N 2021/6439* (2013.01)

(58) Field of Classification Search
CPC .................................................... A01N 43/90
USPC ........................................................ 514/205
See application file for complete search history.

(56) References Cited

U.S. PATENT DOCUMENTS

| | | | |
|---|---|---|---|
| 4,740,459 A | 4/1988 | Chen et al. | |
| 5,338,843 A | 8/1994 | Quante et al. | |
| 5,408,481 A | 4/1995 | Scheps | |
| 5,514,561 A | 5/1996 | Quante et al. | |
| 5,955,604 A | 9/1999 | Tsien et al. | |
| 6,462,070 B1 | 10/2002 | Hasan et al. | |
| 6,727,356 B1 | 4/2004 | Reed et al. | |
| 9,828,622 B2 * | 11/2017 | Hasan | C12Q 1/34 |
| 2003/0035448 A1 | 2/2003 | Yin | |
| 2004/0100999 A1 | 5/2004 | Liu | |
| 2004/0115207 A1 | 6/2004 | Irwin et al. | |
| 2008/0064025 A1 | 3/2008 | Su | |
| 2018/0094292 A1 | 4/2018 | Hasan et al. | |

FOREIGN PATENT DOCUMENTS

| | | |
|---|---|---|
| EP | 2285381 | 12/2015 |
| KR | 10-2008-0074156 | 8/2008 |
| WO | WO 1997/03697 | 2/1997 |
| WO | WO 2005/071096 | 8/2005 |
| WO | WO 2007/059266 | 5/2007 |
| WO | WO 2011/109753 | 9/2011 |

OTHER PUBLICATIONS

Bouvier et al., "A fluorescent peptide substrate for the surface metalloprotease of Leishmanie", Experimental Parasitology, Mar. 1993, 76(2): 146-155.
Cincotta et al., "Novel Benzophenothiazinium Photosensitizers; Preliminary In-Vivo Results," SPIE Proceedings, 1990, 1203: 202-209.
Draganescu et al., "Fhit-nucleotide specificity probed with novel fluorescent and fluorogenic substrates," Journal of Biological Chemistry, Feb. 2000, 275(7): 4555-4560.
Erdem et al., "Rapid, low-cost fluorescent assay of-lactamase-derived antibiotic resistance and related antibiotic susceptibility," Journal of Biomedical Optics, SPIE—International Society for Optical Engineering, Oct. 2014, 19(10): 105007 (11 pages).
Extended European Search Report in European Application No. 15200112.9, dated May 18, 2016, 11 pages.
Gam, "Toward high throughput directed evolution of protease specificity using fluorescence activated cell sorting," Dissertation Presented to the Faculty of the Graduate School of the University of Texas at Austin, May 1, 2004, 187 pages.
International Preliminary Report on Patentability in International Application No. PCT/US2009/002812, dated Nov. 18, 2009, 11 pages.
International Search Report and Written Opinion in Application No. PCT/US2013/039961, dated Sep. 17, 2013, 5 pages.
International Search Report and Written Opinion in International Application No. PCT/US2009/002812, dated Sep. 4, 2009, 12 pages.
Jiang and Mellors, "Membrane protein proteolysis assayed by fluorescence quenching: assay of O-sialoglycoprotein endopeptidase," Analytical Biochemistry, May 1988, 259(1): 8-15.
Papanicolaou et al., "Dicrimination of extended-spectrum beta-lactamases by a novel nitrocefin competition assay," Antimicrobial Agents and Chemotherapy, Nov. 1990, 34(11): 2484-2192.
Rovaldi et al., "Photoactive porphyrin derivative with broad-spectrum activity against oral pathogens", In Vitro Antimicrobial Agents and Chemotherapy, American Society for Microbiology, Dec. 2000, 44(12): 3364-3367.
Supplemental European Search Report for European Application No. 06844370.4 , dated Jan. 3, 2012, 4 pages.

(Continued)

*Primary Examiner* — Nizal S Chandrakumar
(74) *Attorney, Agent, or Firm* — Fish & Richardson P.C.

(57) ABSTRACT

Photoactivatable pesticide compounds and methods for the use thereof in the elimination and detection of pests are provided.

13 Claims, 14 Drawing Sheets

Specification includes a Sequence Listing.

(56) References Cited

OTHER PUBLICATIONS

Ulrich et al., "The Chemistry of fluorescent bodipy dyes: versatility unsurpassed," Angew Chemi Int Ed, Feb. 2008, 47(7): 1184-1201.
Xing et al., "Cell-permeable near-infrared fluorogenic substrates for imaging beta-lactamase activity", Journal of the American Chemical Society, Mar. 2005, 127(12): 4158-4159.
Zeina et al., "Killing of cutaneous microbial species by photodynamic therapy", British Journal of Dermatology, Feb. 2001, 144(2): 274-278.
Zheng et al., "Exploiting a bacterial-drug resistance mechanism: a light-activated construct for the destruction of MRSA", Angewandte Chemie International Edition, Mar. 2009, 48(1): 2148-2151.

* cited by examiner

**Visualization of activated PS and DNA in *Brugia malayi***

Female

Muscle — uterus with embryos — chord

Red = fluorescence of activated PS
Blue = DAPI
Green = propidium iodide

β-LACTAMASE TARGETED PHOTOSENSITIZER FOR PESTICIDE AND PEST DETECTION

CROSS-REFERENCE TO RELATED APPLICATION

This application claims the benefit of U.S. Provisional Application No. 61/663,410, filed on Jun. 22, 2012, the entire contents of which are incorporated herein by reference.

RELATED DISCLOSURES

The subject matter disclosed in this application may be related to the subject matter disclosed in U.S. patent application publication no. US 2010-0016208 A1, published on Jan. 21, 2010, and U.S. patent application publication no. US 2011-0112059 A1, published on May 12, 2011, each of which is hereby expressly incorporated herein in its entirety by reference.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein in their entireties by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), are hereby expressly incorporated herein in their entireties by reference.

BACKGROUND OF THE INVENTION

Human filariasis is a major global health problem. The diseases are caused by infections with parasitic filarial nematode worms leading two related disorders. The nematode species responsible for human lymphatic filariasis (LF) are *Wuchereria bancrofti, Brugia malayi* and to a less extent, *B. timori*, while human onchocerciasis is caused by the related filarial nematode, *Onchocerca volvulus*.

Onchocerciasis is cutaneous, wherein adult worms reside in palpable fibrous nodules, which are a result of inflammation to dead microfilaria (the F1 generation released by adult females after mating). One other aspect of the malady is blindness caused by microfilaria migration and invasion of the cornea, keratitis, retinal lesions and degeneration of the optic nerve. Lymphatic filariasis, on the other hand, is a disease associated with dysfunction of lymphatic tissue and lymphodema, leading to a disease state known as elephantiasis, including hydrocoele.

More than 150 million individuals in 80 countries are infected with parasitic filarial nematode worms responsible for lymphatic filariasis (LF) and onchocerciasis (river blindness), with an estimated 1 billion people at risk of infection, ranking filariasis as one of the major causes of global morbidity.

The life cycle of these parasites requires an arthropod vector; LF is transmitted by both anopheline and culicine mosquitoes whereas *O. volvulus* is transmitted by blackflies (*Simulium* species) (Blacklock, 1926; Mullen and Durden, 2009). Adult worms can live for 10 years or more and the microfilaria released into the blood are picked up by the insect vector during a blood meal, undergo several molts and then are delivered to the human host in a subsequent insect bite wound. The infective larvae undergo several molts and develop into male or female adults, mate and give rise to the microfilaria to continue life cycle. There are several challenges associated with attempts to eliminate filariasis: (1.) there are no macrofiliaricidal (adulticide) drugs available. Control programs rely on sustained delivery of antiparasitic drugs, such as DEC (diethylcarbamazine), albendazole, and ivermectin, which have been the mainline drugs of choice for filariasis control. However, these drugs are not effective adulticides and repeated community-wide doses (as part of MDA, mass drug administration) are required to suppress microfilarial production and reduce transmission.

Likewise, Over time insects have become both more numerous and more destructive to plants, both agriculturally and domestically. A host of small insects attack grasses and forage crops, many of them being so small that they are unnoticed though their aggregate injury is enormous. Larger pests, such as worms, grubs, grasshoppers, flies, boll weevils, bollworms, and ticks are equally dangerous to plant life. In total, the damage to crops and other plants from insect attack represents losses of billions of dollars annually.

Photosensitizers (PS) are light-sensitive compounds which undergo a photochemical reaction after the absorption of light quantum. Such photodynamic compounds have been successfully used for antibacterial photodynamic therapies acting throughout the body. A strength of such photodynamic therapy (PDT) is the broad range of targets hit by the reactive molecular species it produces. Targeting the photoreactivity of PSs through catalysis by parasite-specific enzymes maintains this advantage. Still, the current state of PDT has focused on the targeting of parasite-specific enzymes within the human body.

As such, photodynamic compounds having improved specificity for athropod, nematode, insect and parasite-specific enzymes capable of targeting and killing an insect (or other unwanted organism that produces an enzyme capable of hydrolyzing the construct) such as mosquitoes, biting flies, fruit flies, sand flies, barnacles, crustacea, and cockroaches, outside of the human body, would be desirable.

SUMMARY OF THE INVENTION

The invention provides, inter alia, novel methods to control and/or kill arthropods, nematodes, insects and parasites in plant and animal (e.g., human) hosts via the targeted release of free photosensitizer from a quenched to an unquenched and active state by ß-lactamases that are produced by the insect. The invention is based, at least in part, on the discovery that when a pest, e.g., an insect, ingests an enzyme-cleavable ß-lactamase specific construct, the construct is cleaved by ß-lactamases that are produced by the insect, resulting in the release of free photosensitizer within the insect. When the insect is then exposed to light, the free photosensitizer is converted to a phototoxic species that kills the insect. In certain advantageous embodiments, the insect also fluoresces as a result of the cleavage allowing for insect detection via fluorescence emission.

Thus, in one aspect, the invention provides a pesticidal composition comprising a pesticidally effective amount of one or more photosensitizers that are linked by one or more moieties cleavable by ß-lactamase, wherein the linked photosensitizers are present in an amount sufficient to quench photoactivation of the photosensitizers and wherein said one or more photosenitizers are capable of generating a phototoxic species upon dequenching and light-activation.

In yet another aspect, the invention provides a pesticidal composition comprising pesticidally effective amount of one or more photosensitizers and one or more binders effective to quench photoactivation, wherein the photosensitizers are connected to the binder through one or more moieties cleavable by a ß-lactamase expressed by a pest and wherein said one or more photosenitizers are capable of generating a phototoxic species upon dequenching and light-activation. In a further embodiment, the binder is a fluorophore.

In yet another aspect, the invention provides a pesticidal composition comprising a backbone coupled to one or more photosensitizers and one or more binders effective to quench photoactivation, wherein the binders are connected to the backbone through one or more moieties cleavable by a ß-lactamase expressed by a pest and wherein said one or more photosenitizers are capable of generating a phototoxic species upon dequenching and light-activation.

In yet another aspect, the invention provides a pesticidal composition comprising a backbone coupled to a plurality of photosensitizers and one or more binders effective to quench photoactivation, wherein the photosensitizers are connected to the backbone through one or more moieties cleavable by ß-lactamase.

In accordance with the invention, the pest is an animal that expresses ß-lactamase. In particular embodiments, the pest is an animal that expresses a ß-lactamase comprising the protein domain sequence:

```
                                       (SEQ ID NO: 1)
ILTEKRKILVDCGDPWNGTQIIQALSKYSLNCDDITDLIITHGHSDHCGN

LSLFQQAKIYMGDDMAKDGIYEGIWTLDDFVKIRPTPGHTDRSIIVLDTE

YGTVAIVGDIFEEENDDDSWKENSKYPEEQQKSRKIILKEADWIIPGH (GenBANK protein sequence XP_001891895)
``` or a fragment thereof.

In certain embodiments, the pest expresses a ß-lactamase comprising a protein domain sequence having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, identity (e.g., when compared to the overall length of the protein sequence) to SEQ ID NO:1 or a fragment thereof.

In still other embodiments, the pest is an animal that expresses a ß-lactamase comprising the protein domain sequence:

```
                                       (SEQ ID NO: 2)
TNTYIIGTGKRRILLDAGDENVPEYIGHLKKVISDERILINDIIVSHWHH

DHIGGVDEVLDIIENKDSCKVWKFPRADAPDGTIRNANINHLKHGQKFNI

EGATLEVLHTPGHTTDHVVLVLHEDNSLFSADCILGEGSTVFEDLYEYTK

SLQAIQDAKPSVIYPG (GenBANK protein sequence

XP_001656361)
``` or a fragment thereof.

In certain embodiments, the pest expresses a ß-lactamase comprising a protein domain sequence having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, identity (e.g., when compared to the overall length of the protein sequence) to SEQ ID NO:2 or a fragment thereof.

In certain embodiments, the host is an animal, e.g., human.

In other embodiments the host is a plant. Plants in accordance with the invention include, but are not limited to corn, maize, wheat, tobacco, cotton, rice, soybean, peanut, sugarcane, hay, sorghum, lettuces, kales, cabbages, fruit trees, or horitcultural flowers.

In embodiment embodiments, the pests targeted in plants include, but are not limited to, nematodes, grubs, weevils, borers, aphids, moths, mosquitoes, flies, ticks, termites, beetles, caterpillar, cutworms, earworms, armyworms, or budworms.

In certain embodiments, the photosensitizer is a porphyrin. The porphyrin can be, but is not limited to, a porfimer sodium, hematoporphyrin IX, hematoporphyrin ester, dihematoporphyrin ester, synthetic diporphyrin, O-substituted tetraphenyl porphyrin, 3,1-meso tetrakis porphyrin, hydroporphyrin, benzoporphyrin derivative, benzoporphyrin monoacid derivative, monoacid ring derivative, tetracyanoethylene adduct of benzoporphyrin, dimethyl acetylenedicarboxylate adduct of benzoporphyrin, δ-aminolevulinic acid, benzonaphthoporphyrazine, naturally occurring porphyrin, ALA-induced protoporphyrin IX, synthetic dichlorin, bacteriochlorin tetra(hydroxyphenyl) porphyrin, purpurin, octaethylpurpurin derivative, etiopurpurin, tin-etiopurpurin, porphycene, chlorin, chlorin $e_6$, mono-l-aspartyl derivative of chlorin $e_6$, di-l-aspartyl derivative of chlorin $e_6$, tin(IV) chlorin $e_6$, meta-tetrahydroxyphenylchlorin, chlorin $e_6$ monoethylendiamine monamide, verdin, zinc methyl pyroverdin, copro II verdin trimethyl ester, deuteroverdin methyl ester, pheophorbide derivative, pyropheophorbide, texaphyrin, lutetium (III) texaphyrin, or gadolinium(III) texaphyrin.

In other embodiments, the photosensitizer is a photoactive dye. The photoactive dye includes, but is not limited to, a merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (EtNBS), phenothiazine derivative, phenothiaziniums such as rose Bengal, toluidine blue derivatives, toluidine blue O (TBO), methylene blue (MB), new methylene blue N (NMMB), new methylene blue BB, new methylene blue FR, 1,9-dimethylmethylene blue chloride (DMMB), methylene blue derivatives, methylene green, methylene violet Bemthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, or thionine.

In still other embodiments, the photosensitizer includes, but is not limited to, a Diels-Alder adduct, dimethyl acetylene dicarboxylate adduct, anthracenedione, anthrapyrazole, aminoanthraquinone, phenoxazine dye, chalcogenapyrylium dye, cationic selena, tellurapyrylium derivative, cationic imminium salt, or tetracycline.

In yet another embodiment, the photosensitizer composition comprises a plurality of the same photosensitizer.

In one embodiment, the moiety cleavable by ß-lactamase of the photosensitizer composition comprises a cephalosporin, a penicillin, a penem, a carbapenem, a monocyclic monobactem, or a fragment thereof. In a further embodiment, the moiety cleavable by ß-lactamase of the photosensitizer composition comprises a cephalosporin, a penicillin, or a fragment thereof. The cephalosporin or penicillin fragment can comprise a beta-lactam ring, and the enzyme cleavage site can be cleaved by a lactamase. In another embodiment, the moiety cleavable by ß-lactamase is a cephalosporin. At least one photosensitizer can be bound at the 3' position of the cephalosporin.

In yet another embodiment, a binder is present and connected to the photosensitizer by one or more moieties cleavable by ß-lactamase. In specific embodiments, binder can be a fluorophore or an other photosensitizer.

In yet another aspect, the invention provides a pharmaceutical composition comprising a pesticidally effective amount of a photosensitizer composition of the invention and a pharmaceutically acceptable excipient or carrier.

In yet another aspect, the invention provides a method of eliminating a pest from a host, the method comprising the steps of: contacting the pest with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby eliminating the pest from the host.

In certain embodiments, phototoxic species is also flourescent.

In other embodiments, the pest is an arthropod, a nematode or an insect and the host is a plant. In some embodiments, the pest is selected from the group consisting of nematodes, grubs, weevils, borers, aphids, moths, mosquitoes, flies, ticks, termites, beetles, caterpillar, cutworms, earworms, armyworms, and budworms. In other embodiments, the plant is selected from the group consisting of corn, maize, wheat, tobacco, cotton, rice, soybean, peanut, sugarcane, hay, sorghum, lettuces, kales, cabbages, fruit trees, and horitcultural flowers.

In still other embodiments, the pest is a parasite and the host is an animal or human. In some embodiments, the parasite is selected from the group consisting of ticks, lice, mites, ascarids, filarias, hookworms, pinworms, whipworms, strongyles, *Trichinella spiralis, Dirofilaria immitis, Haemonchus contortus, Brugia malayi* and *Myrmeconema neotropicum*.

In another aspect, the invention provides a method for eliminating a pest from an industrial material, the method comprising the steps of: contacting the pest with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby eliminating the pest from said host.

In certain embodiments, the pest is selected from the group consisting of beetles, termites, and hymenopterons.

In other embodiments, the industrial material is selected from the group consisting of plastics, adhesives, sizes, paper and card, leather, wood and processed wood products.

In another aspect, the invention provides a method for eliminating a pest from an enclosed space, the method comprising the steps of: contacting the pest with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby eliminating the pest from said space.

In some embodiments, the pest is selected from the group consisting of scorpions, spiders, woodlice, pillbugs, bedbugs, millipedes, centipedes, caterpillars, moths, silverfish, cockroaches, grasshoppers, locusts, flies and mosquitoes.

In another aspect, the invention provides a method for detecting a pest, said method comprising the steps of: contacting the pest with a quenched photosensitizer composition comprising a plurality of photosensitizers that are linked by one or more moieties cleavable by a ß-lactamase expressed by the pest, wherein said linked photosensitizers are present in an amount sufficient to quench photoactivation of said photosensitizers; cleaving one or more moieties cleavable by the ß-lactamase to dequench the photosensitizer composition; and light-activating the composition to produce a fluorescent species, and detecting the pest by observing the fluorescence, thereby detecting the presence of the pest.

In some embodiments, the florescent species is also phototoxic.

In another aspect, the invention provides a method for controlling an insect pest, the method comprising the steps of: contacting the pest with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby controlling said insect pest.

In certain embodiments, the insect is *Aedes albopictus*.

In another aspect, the invention provides a method for controlling a filarial nematode, the method comprising the steps of: contacting the worm with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby controlling said worm.

In certain embodiments, the filarial nematode is *Wuchereria bancrofti, Brugia malayi*, or *B. timori*.

In another aspect, the invention provides a method for ameliorating filariasis in a subject, the method comprising the steps of: administering to the subject an effective amount of a composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby ameliorating filariasis.

In some embodiments, the filariasis is associated with *Wuchereria bancrofti, Brugia malayi*, and/or *B. timori*.

In certain embodiments, the method reduces the filarial load in the subject by at least about 10-25% or more.

In another aspect, the invention provides a method for controlling a fouling pest on an object in contact with saltwater or brackish water, the method comprising the steps of: contacting the pest with an effective amount of a pesticidal composition comprising one or more photosensitizers that are linked by one or more moieties cleavable by a ß-lactamase expressed by the pest, wherein the one or more moieties cleavable by the ß-lactamase comprises an enzyme cleavage site for an enzyme of a pathogen, and optionally one or more binders, and wherein the linked photosensitizers are present in an amount sufficient to quench photoactivation of the photosensitizers; cleaving one or more moieties cleavable by the ß-lactamase to dequench the photosensitizer composition and light-activating the composition to produce a phototoxic species, thereby controlling the pest.

In certain embodiments, the fouling pest is a goose barnacle, an acorn barnacle or a sessile Oligochaeta.

Methods of the invention may further comprise the step of obtaining the photosensitizer composition, linker or binder.

The light-activation in the methods of the invention may be from exposure to sunlight, administration of LED lighting, or administration of laser lighting.

In yet another aspect, the invention provides a kit for eliminating a pest the comprising a pesticidal composition of the invention and instructions for using the pesticidal composition to eliminate the pest in accordance with the methods of the invention.

In yet another aspect, the invention provides a kit for detecting a pest the a photosensitizer composition comprising one or more photosensitizers that are linked by one or more moieties cleavable by a ß-lactamase expressed by the pest, wherein said linked moieties are present in an amount sufficient to quench photoactivation of said photosensitizers and wherein said one or more photosenitizers are capable of generating a fluorescent species upon dequenching and light-activation, and instructions for using the photosensitizer composition to detect the pest.

Other aspects of the invention are described in the following disclosure, and are within the ambit of the invention.

BRIEF DESCRIPTION OF THE FIGURES

Various advantageous features and embodiments of the present invention are described below with reference to the accompanying drawings in which.

DETAILED DESCRIPTION OF THE INVENTION

Figure 1:
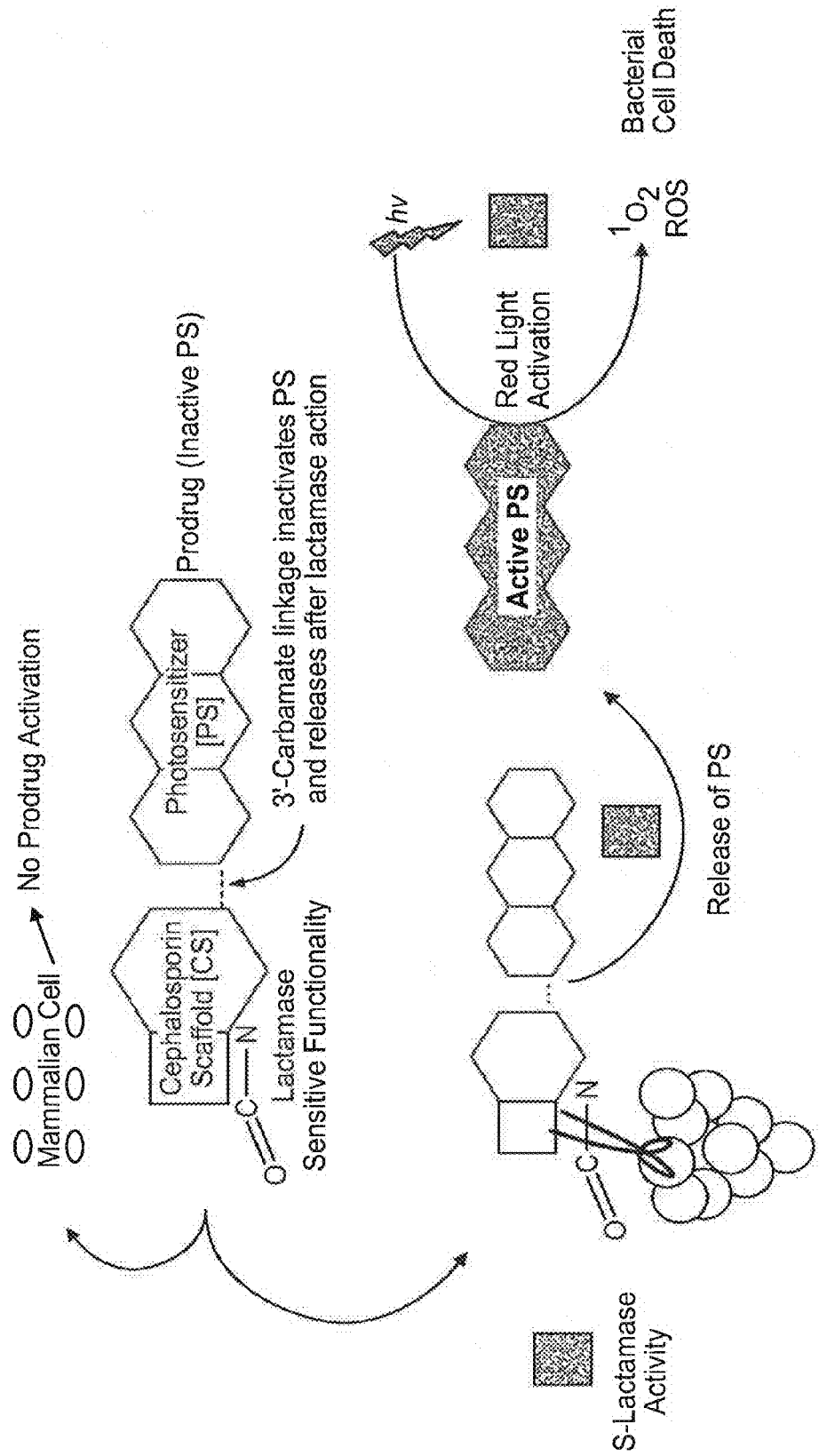
FIG. 1 schematically depicts the development of a carbamate-linked photosensitizer (PS) that is inactive (with or without light) while linked and is light-activatable only when released by the β-lactamase enzyme-mediated cleavage.

The following Detailed Description, given by way of example, but not intended to limit the invention to specific embodiments described, may be understood in conjunction with the foregoing drawings and the following non-limiting definitions that are given by way of example to facilitate understanding of the invention.

I. Definitions

The term "photosensitizer" refers to a photoactivatable compound, or a biological precursor thereof, that produces a reactive species (e.g., oxygen) having a photochemical (e.g., cross linking) or phototoxic effect on a cell, cellular component or biomolecule. As used herein, a photosensitizer refers to a substance which, upon irradiation with electromagnetic energy of the appropriate wavelength (e.g., light), produces a cytotoxic effect.

As used herein, the term "fluorescent dye" refers to dyes that are fluorescent when illuminated with light but do not produce reactive species that are phototoxic or otherwise capable of reacting with biomolecules. A photosensitizer will fluoresce when illuminated with a certain wavelength and power of light and also produce reactive species that is phototoxic under the same or different wavelength and power of light. The term "photoactive dye," as used herein, means that the illuminated photosensitizer produces a fluorescent species, but not necessarily a reactive species in phototoxic amounts (i.e., a phototoxic species). Depending on the wavelength and power of light administered, a photosensitizer can be activated to fluoresce and, therefore, act as a photoactive dye, but not produce a phototoxic species. The wavelength and power of light can be adapted by methods known to those skilled in the art to bring about a phototoxic effect where desired.

As used herein, the term "backbone" refers to an agent that functions to couple one or more components of a photosensitizer composition of the invention, such as, for example, a polyamino acid or like agent that is linked to one or more photosensitizers and/or one or more binders and/or one or more targeting moieties The backbone itself additionally can be a targeting moiety, e.g. polylysine. A "backbone" as used herein is as a moiety higher in molecular weight and capable of loading more photoactive molecules than a 'linker'. Backbone can be a polymeric structure which provides a base to add multiple units (more than three). Examples of backbones that can be used according to the invention, include, but are not limited to polyethylene glycol and polyproline.

As used herein, the term "linker" or "moiety cleavable by ß-lactamase" refers to an agent capable of linking two components of the photosensitizer composition together (e.g., a photosensitizer to another photosensitizer, a photosensitizer to a binder, a photosensitizer to a backbone, or a binder to a backbone).

As used herein, the term "binder" refers to an agent that absorbs energy from an adjacent, activated photosensitizer or otherwise inactivates the photosensitizer, and, thus, quenches the photosensitizer.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. Accordingly, the term is intended to include any gene encoding a β-lactamase.

As used herein, the terms "peptide", "polypeptide", and "protein" are, unless specified otherwise, used interchangeably. Peptides, polypeptides, and proteins used in methods and compositions described herein can be recombinant, purified from natural sources, or chemically synthesized. For example, reference to the use of a bacterial protein or a protein from bacteria, includes the use of recombinantly produced molecules, molecules purified from natural sources, or chemically synthesized molecules.

The term "plurality" refers to at least two, preferably at least about 10 and even more preferably, at least about 20 or more photosensitizer or binder molecules present in a composition of the invention.

The term "host" is used herein to include both living hosts and non-living/inanimate hosts. Examples of living hosts include plants and animals. e.g., humans. Non-living/inanimate hosts include industrial sites, public areas, and man-made surfaces including household surfaces (kitchen surfaces, floors, walls, ceilings, etc.), patios and the like.

The term "animal" is used herein to refer to a living animal, including a human, that carries an unwanted organism, the unwanted organism being the target of the methods described herein.

The term "plant" is used herein to refer to any plant including, but not limited to agricultural crops, fruit trees, nut trees, domestic crops, and flowers. Such plants and crops include, but are not limited to, corn, maize, wheat, tobacco, cotton, rice, soybean, peanut, sugarcane, hay, sorghum, lettuces, kales, cabbages, apples, oranges, pears, pumpkins, tomatoes, fruit trees, or horitcultural flowers.

As used herein, "pest" or "target organism" means an animal, e.g., insect, parasite or otherwise, that expresses a ß-lactamase capable of cleaving the moieties which bind the photosensitizers in the compositions of the inventions. Such pests include any pest that adversely impacts on the health and productivity of plants or other animals, or compromises the integrity of an industrial material or dwelling. Specific pests include, but are not limited to, nematodes, grubs, weevils, borers, aphids, moths, mosquitoes, flies, ticks, termites, beetles, caterpillar, cutworms, earworms, armyworms, or budworms. In one embodiment, the mosquito is *Aedes albopictus*.

As used herein, the term "parasite" includes an animal organism that lives in or on another and takes its nourishment from that other organism. Parasites in accordance with the invention include, e.g., protozoa, nematodes, helminths and arthropods. Parasites in accordance with the invention further include symbiotic animal organisms. In one embodiment, the parasite is *Brugia malayi*. Methods of the invention include controlling or eliminating *Brugia malayi* from a human or insect host (e.g., *Aedes albopictus*).

Figure 7:
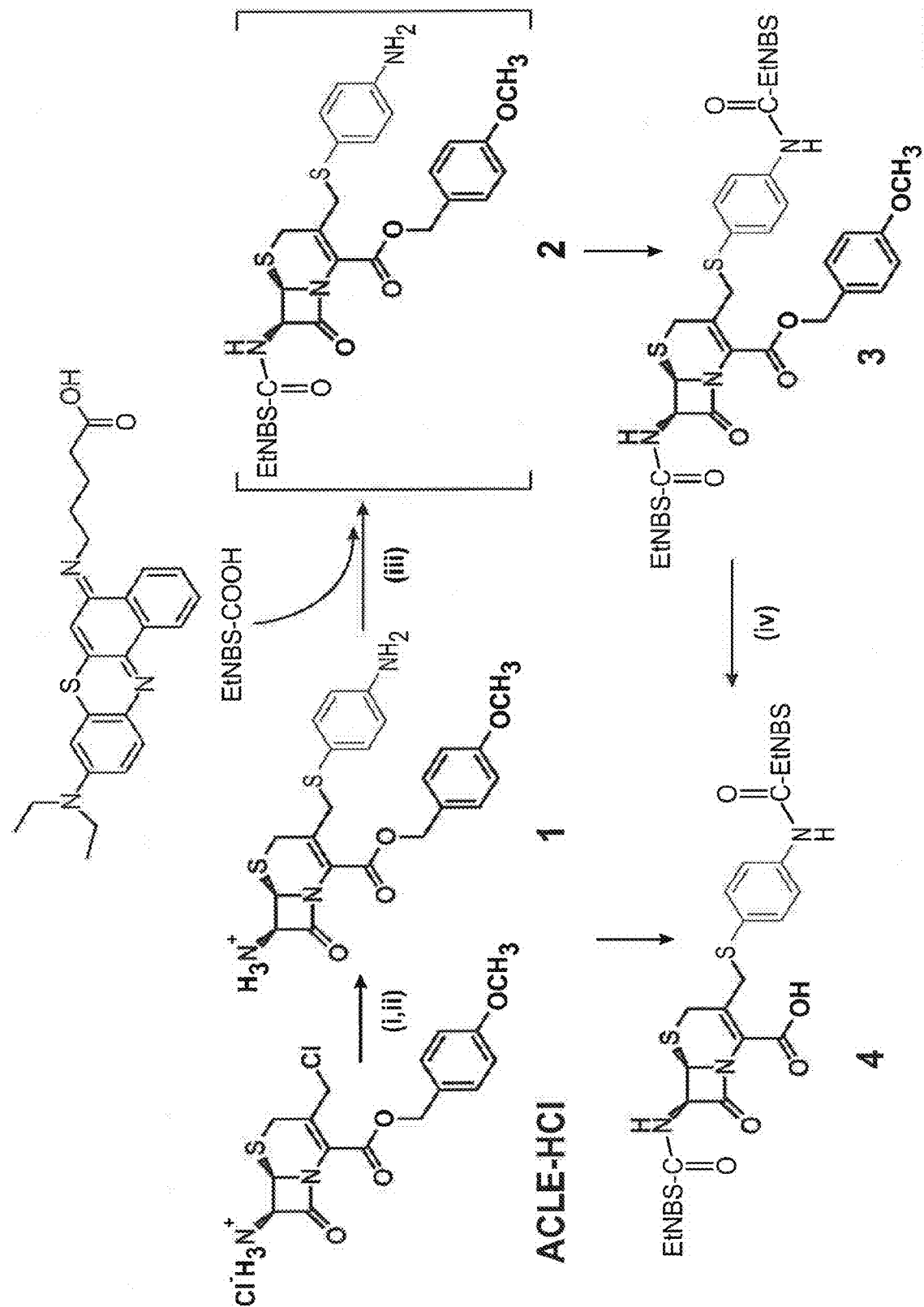
FIG. 7 shows the synthesis of β-LEAP

As used herein, the term "pesticidally effective amount" refers to that amount of a photosensitizer composition that, when administered to or ingested by a pest, is sufficient to eliminate, terminate or otherwise control the pest. Thus, e.g., a pesticidally effective amount of a photosensitizer composition as described herein is a quantity sufficient to result in the death of a pest so that the adverse effects of the pest are reduced or alleviated. In one embodiment, a composition of the invention comprises an effective amount of a prodrug construct with a photosensitizer and a quencher linked by a beta-lactam ring, resulting in a diminished phototoxicity. This construct is referred to as beta-lactamase enzyme-activated-photosensitizer (β-LEAK The synthesis of β-LEAP is provided at FIG. 7.

As used herein, the term "control" is meant reducing the survival, proliferation, or reproduction of a pest. Such reduction may be by at least about 10%, 25%, 50%, 75% or more. In one embodiment, a composition of the invention ameliorates or controls a parasite infestation (for example, as in filariasis) by reducing the parasitic load in a subject by at least about 5, 10, 50, 75 or 100%.

As used herein, a "peptide antibiotic" is a linear or cyclic oligopeptide, or an active fragment, or analog thereof, which possesses antibiotic activity against bacterial or fungal species, and which is synthesized enzymatically on a multi-protein complex to which it is attached by a thioether bond. A peptide antibiotic may include non-ribosomal amino acids such as D amino acids, and may include non-amino acid residues such as esters of lactic acid or valeric acid.

The term "obtaining" as in "obtaining" the "photosensitizer composition," "linker" or "binder," is intended to include purchasing, synthesizing or otherwise acquiring the elements of the invention.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

II. Compositions of the Invention

A. Photosensitizers

Photosensitizers known in the art are typically selected for use according to: 1) efficacy in delivery, 2) proper localization in target tissues, 3) wavelengths of absorbance, 4) proper excitatory wavelength, 5) purity, and 6) in vivo effects on pharmacokinetics, metabolism, and reduced toxicity.

A photosensitizer for clinical use is optimally amphiphilic, meaning that it shares the opposing properties of being water-soluble, yet hydrophobic. The photosensitizer should be water-soluble in order to pass through the bloodstream systemically, however it should also be hydrophobic enough to pass across cell membranes. Modifications, such as attaching polar residues (amino acids, sugars, and nucleosides) to the hydrophobic porphyrin ring, can alter polarity and partition coefficients to desired levels. Such methods of modification are well known in the art.

In specific embodiments, photosensitizers of the present invention absorb light at a relatively long wavelength, thereby absorbing at low energy. Low-energy light can travel further through tissue than high-energy light, which becomes scattered. Optimal tissue penetration by light occurs between about 650 and about 800 nm. Porphyrins found in red blood cells typically absorb at about 630 nm, and new, modified porphyrins have optical spectra that have been "red-shifted", in other words, absorbs lower energy light. Other naturally occurring compounds have optical spectra that is red-shifted with respect to porphyrin, such as chlorins found in chlorophyll (about 640 to about 670 nm) or bacteriochlorins found in photosynthetic bacteria (about 750 to about 820 nm).

Photosensitizers of the invention can be any known in the art, and optionally coupled to molecular carriers.

i) Porphyrins and Hydroporphyrins

Porphyrins and hydroporphyrins can include, but are not limited to, Photofrin®® (porfimer sodium), hematoporphyrin IX, hematoporphyrin esters, dihematoporphyrin ester, synthetic diporphyrins, O-substituted tetraphenyl porphyrins (picket fence porphyrins), 3,1-meso tetrakis (o-propionamido phenyl) porphyrin, hydroporphyrins, benzoporphyrin derivatives, benzoporphyrin monoacid derivatives (BPD-MA), monoacid ring "a" derivatives, tetracyanoethylene adducts of benzoporphyrin, dimethyl acetylenedicarboxylate adducts of benzoporphyrin, endogenous metabolic precursors, δ-aminolevulinic acid, benzonaphthoporphyrazines, naturally occurring porphyrins, ALA-induced protoporphyrin IX, synthetic dichlorins, bacteriochlorins of the tetra (hydroxyphenyl) porphyrin series, purpurins, tin and zinc derivatives of octaethylpurpurin, etiopurpurin, tin-etio-purpurin, porphycenes, chlorins, chlorin $e_6$, mono-l-aspartyl derivative of chlorin $e_6$, di-l-aspartyl derivative of chlorin $e_6$, tin(IV) chlorin $e_6$, meta-tetrahydroxyphenylchlorin, chlorin $e_6$ monoethylendiamine monamide, verdins such as, but not limited to zinc methyl pyroverdin (ZNMPV), copro II verdin trimethyl ester (CVTME) and deuteroverdin methyl ester (DVME), pheophorbide derivatives, and pyropheophorbide compounds, texaphyrins with or without substituted lanthanides or metals, lutetium (III) texaphyrin, and gadolinium (III) texaphyrin.

Porphyrins, hydroporphyrins, benzoporphyrins, and derivatives are all related in structure to hematoporphyrin, a molecule that is a biosynthetic precursor of heme, which is the primary constituent of hemoglobin, found in erythrocytes. First-generation and naturally occurring porphyrins are excited at about 630 nm and have an overall low fluorescent quantum yield and low efficiency in generating reactive oxygen species. Light at about 630 nm can only penetrate tissues to a depth of about 3 mm, however there are derivatives that have been 'red-shifted' to absorb at longer wavelengths, such as the benzoporphyrins BPD-MA (Verteporfin). Thus, these 'red-shifted' derivatives show less collateral toxicity compared to first-generation porphyrins.

Chlorins and bacteriochlorins are also porphyrin derivatives, however these have the unique property of hydrogenated exo-pyrrole double bonds on the porphyrin ring backbone, allowing for absorption at wavelengths greater than about 650 nm. Chlorins are derived from chlorophyll, and modified chlorins such as meta-tetra hydroxyphenylchlorin (mTHPC) have functional groups to increase solubility. Bacteriochlorins are derived from photosynthetic bacteria and are further red-shifted to about 740 nm. A specific embodiment of the invention uses chlorin$_{e6}$.

Purpurins, porphycenes, and verdins are also porphyrin derivatives that have efficacies similar to or exceeding hematoporphyrin. Purpurins contain the basic porphyrin macrocycle, but are red-shifted to about 715 nm. Porphycenes have similar activation wavelengths to hematoporphyrin (about 635 nm), but have higher fluorescence quantum yields. Verdins contain a cyclohexanone ring fused to one of the pyrroles of the porphyrin ring. Phorbides and pheophorbides are derived from chlorophylls and have 20 times the effectiveness of hematoporphyrin. Texaphyrins are new metal-coordinating expanded porphyrins. The unique feature of texaphyrins is the presence of five, instead of four, coordinating nitrogens within the pyrrole rings. This allows for coordination of larger metal cations, such as trivalent lanthanides. Gadolinium and lutetium are used as the coordinating metals. In a specific embodiment, the photosensitizer can be Antrin®, otherwise known as motexafin lutetium.

5-aminolevulinic acid (ALA) is a precursor in the heme biosynthetic pathway, and exogenous administration of this compound causes a shift in equilibrium of downstream reactions in the pathway. In other words, the formation of the immediate precursor to heme, protoporphyrin IX, is dependent on the rate of 5-aminolevulinic acid synthesis, governed in a negative-feedback manner by concentration of free heme. Conversion of protoporphyrin IX is slow, and where desired, administration of exogenous ALA can bypass the negative-feedback mechanism and result in accumulation of phototoxic levels of ALA-induced protoporphyrin IX. ALA is rapidly cleared from the body, but like hematoporphyrin, has an absorption wavelength of about 630 nm.

First-generation photosensitizers are exemplified by the porphyrin derivative Photofrin®, also known as porfimer sodium. Photofrin® is derived from hematoporphyrin-IX by acid treatment and has been approved by the Food and Drug Administration for use in PDT. Photofrin® is characterized as a complex and inseparable mixture of monomers, dimers, and higher oligomers. There has been substantial effort in the field to develop pure substances that can be used as successful photosensitizers. Thus, in a specific embodiment, the photosensitizer is a benzoporphyrin derivative ("BPD"), such as BPD-MA, also commercially known as Verteporfin. U.S. Pat. No. 4,883,790 describes BPDs. Verteporfin has been thoroughly characterized (Richter et al., 1987; Aveline et al., 1994; Levy, 1994) and it has been found to be a highly potent photosensitizer for PDT. Verteporfin has been used in PDT treatment of certain types of macular degeneration, and is thought to specifically target sites of new blood vessel growth, or angiogenesis, such as those observed in "wet" macular degeneration. Verteporfin is typically administered intravenously, with an optimal incubation time range from 1.5 to 6 hours. Verteporfin absorbs at 690 nm, and is activated with commonly available light sources. One tetrapyrrole-based photosensitizer having recent success in the clinic is MV0633 (Miravant).

In specific embodiments, the photosensitizer has a chemical structure that includes multiple conjugated rings that allow for light absorption and photoactivation. Such specific embodiments include motexafin lutetium (Antrin®) and $chlorin_{e6}$.

ii) Cyanine and Other Photoactive Dyes

Cyanine and other dyes include but are not limited to a merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure chloride, benzophenothiazinium, benzophenothiazinium chloride (EtNBS), phenothiazine derivative, phenothiaziniums such as rose Bengal, toluidine blue derivatives, toluidine blue O (TBO), methylene blue (MB), new methylene blue N (NMMB), new methylene blue BB, new methylene blue FR, 1,9-dimethylmethylene blue chloride (DMMB), methylene blue derivatives, methylene green, methylene violet Bernthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, or thionine.

Cyanines are deep blue or purple compounds that are similar in structure to porphyrins. However, these dyes are much more stable to heat, light, and strong acids and bases than porphyrin molecules. Cyanines, phthalocyanines, and naphthalocyanines are chemically pure compounds that absorb light of longer wavelengths than hematoporphyrin derivatives with absorption maxima at about 680 nm. Phthalocyanines, belonging to a new generation of substances for PDT are chelated with a variety of diamagnetic metals, chiefly aluminum and zinc, which enhance their phototoxicity. A ring substitution of the phthalocyanines with sulfonated groups will increase solubility and affect the cellular uptake. Less sulfonated compounds, which are more lipophilic, show the best membrane-penetrating properties and highest biological activity. The kinetics are much more rapid than those of HPD, where, for example, high tumor to tissue ratios (8:1) were observed after 1-3 hours. The cyanines are eliminated rapidly and almost no fluorescence can be seen in the tissue of interest after 24 hours.

Other photoactive dyes such as methylene blue and rose bengal, are also used for photodynamic therapy. Methylene blue is a phenothiazine cationic dye that is exemplified by its ability to specifically target mitochondrial membrane potential. Rose-bengal and fluorescein are xanthene dyes that are well documented in the art for use in photodynamic therapy. Rose bengal diacetate is an efficient, cell-permeant generator of singlet oxygen. It is an iodinated xanthene derivative that has been chemically modified by the introduction of acetate groups. These modifications inactivate both its fluorescence and photosensitization properties, while increasing its ability to cross cell membranes. Once inside the cell, esterases remove the acetate groups and restore rose bengal to its native structure. This intracellular localization allows rose bengal diacetate to be a very effective photosensitizer.

iii) Other Photosensitizers

Diels-Alder adducts, dimethyl acetylene dicarboxylate adducts, anthracenediones, anthrapyrazoles, aminoanthraquinone, phenoxazine dyes, chalcogenapyrylium dyes such as cationic selena and tellurapyrylium derivatives, cationic imminium salts, and tetracyclines are other compounds that also exhibit photoactive properties and can be used advantageously in photodynamic therapy. Other photosensitizers that do not fall in either of the aforementioned categories have other uses besides photodynamic therapy, but are also photoactive. For example, anthracenediones, anthrapyrazoles, aminoanthraquinone compounds are often used as anticancer therapies (i.e. mitoxantrone, doxorubicin). Chalcogenapyrylium dyes such as cationic selena- and tellurapyrylium derivatives have also been found to exhibit photoactive properties in the range of about 600 to about 900 nm range, more preferably from about 775 to about 850 nm. In addition, antibiotics such as tetracyclines and fluoroquinolone compounds have demonstrated photoactive properties.

B. Linkers/Moieties Cleavable by ß-Lactamase

Linkers of the invention are capable of linking two components of the photosensitizer composition together (e.g., a photosensitizer to another photosensitizer, a photosensitizer to a binder, a photosensitizer to a backbone, or a binder to a backbone). Any bond which is capable of linking the components such that they are stable under physiological conditions for the time needed for administration, ingestion by the pest and activation within the pest is suitable, but covalent linkages are preferred. The link between two components may be direct, e.g., where a photosensitizer is linked directly to another photosensitizer, or indirect, e.g., where a photosensitizer is linked to an intermediate, e.g., linked to a backbone, and that intermediate is linked to another photosensitizer. A linker should function under conditions of temperature, pH, salt, solvent system, and other reactants that substantially retain the chemical stability of the photosensitizer and the backbone (if present).

Linkers according to the invention comprise moieties cleavable by a ß-lactamase enzyme. In one aspect of the invention, linker cleavage by a ß-lactamase causes reduction of the quenching that results from the conformation adopted by the multiple photosensitizers linked to one another. In another aspect, linker cleavage by ß-lactamase causes reduction of the quenching that results from inclusion of a binder.

A linker can link components without the addition to the linked components of elements of the linker. Other linkers result in the addition of elements of the linker to the linked components. For example, linkers can be cross-linking agents that are homo- or hetero-bifunctional, and wherein one or more atomic components of the agent can be retained in the composition.

Many linkers react with an amine and a carboxylate, to form an amide, or an alcohol and a carboxylate to form an ester. Linkers are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, N.Y. Linkers should link component moieties stably, but such that there is only minimal or no denaturation or deactivation of the photosensitizer or other linked component.

The pesticidal compositions of the invention can be prepared by linking the photosensitizers to one another or to other components using methods known in the art. A variety of linkers, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl) cyclohexane-1-carboxylate (sulfo-SMCC) (Karpovsky et al. (1984) J. Exp. Med. 160:1686; Liu, M A et al. (1985) Proc. Natl. Acad. Sci. USA 82:8648). Other methods include those described by Paulus and Behring (1985) Ins. Mitt., 78:118-132; Brennan et al. (1985) Science 229:81-83 and Glennie et al., (1987) J. Immunol, 139:2367-2375. A large number of linkers for peptides and proteins, along with buffers, solvents, and methods of use, are described in the Pierce Chemical Co. catalog, pages T-155 to T-200, 1994 (3747 N. Meridian Rd., Rockford Ill., 61105, U.S.A.; Pierce Europe B.V., P.O. Box 1512, 3260 BA Oud Beijerland, The Netherlands), the contents of which are hereby incorporated by reference.

DCC is a useful linker (Pierce #20320; Rockland, Ill.). DCC (N,N'-dicyclohexylcarbodiimide) is a carboxy-reactive cross-linker commonly used as a linker in peptide synthesis. Another useful cross-linking agent is SPDP (Pierce #21557), a heterobifunctional cross-linker for use with primary amines and sulfhydryl groups. SPDP produces cleavable cross-linking such that, upon further reaction, the agent is eliminated, so the photosensitizer can be linked directly to a backbone or molecular carrier. Other useful linking agents are SATA (Pierce #26102) for introduction of blocked SH groups for two-step cross-linking (Pierce #26103), and sulfo-SMCC (Pierce #22322), reactive towards amines and sulfhydryls. Other cross-linking and coupling agents are also available from Pierce Chemical Co. (Rockford, Ill.).

Additional useful linking agents are hydrazines or hydrazine derivatives, compounds that are very soluble in water and soluble in alcohol. Hydrazines are corrosive and strong reducing agents, though they constitute weaker bases than ammonia. Hydrazines are dibasic and form many salts, e.g., mono- and di-hydrochlorides, mono- and di-nitrates, and two sulfates. The hydrazine resin has been found to be a novel and highly useful platform for polyamide synthesis. The hydrazine resin is stable to elevated coupling temperatures, yet is cleaved rapidly at moderate temperatures by a wide range of nucleophiles following a mild and selective oxidation protocol.

Additional compounds and processes, particularly those involving a Schiff base as an intermediate, for conjugation of proteins to other proteins or to other compositions, for example, to reporter groups or to chelators for metal ion labeling of a protein, are disclosed in EP 243,929 A2 (published Nov. 4, 1987).

Photosensitizers which contain carboxyl groups can be joined to lysine s-amino groups in target polypeptides either by preformed reactive esters (such as N-hydroxy succinimide ester) or esters conjugated in situ by a carbodiimide-mediated reaction. The same applies to photosensitizers that contain sulfonic acid groups, which can be transformed to sulfonyl chlorides, which react with amino groups. Photosensitizers that have carboxyl groups can be joined to amino groups on the polypeptide by an in situ carbodiimide method or by hydrazine or hydrazine derivatives. Photosensitizers can also be attached to hydroxyl groups, of serine or threonine residues or to sulfhydryl groups, of serine or threonine residues or to sulfhydryl groups of cysteine residues.

Methods of joining components of a composition can use heterobifunctional cross linking reagents. These agents bind a functional group in one chain and a different functional group in a second chain. These functional groups typically are amino, carboxyl, sulfhydryl, and aldehyde. There are many permutations of appropriate moieties that will react with these groups and with differently formulated structures, to join them together (described in the Pierce Catalog and Merrifield et al. (1994) Ciba Found Symp. 186:5-20).

Generally, the photosensitizer compositions of the invention can be prepared by linking the photosensitizer to another photosensitizer, a binder and/or a backbone using methods described in the following Examples or by methods known in the art. A variety of linkers can be used for covalent conjugation.

Yield from linking reactions can be assessed by spectroscopy of product eluting from a chromatographic fractionation in the final step of purification. The presence of unlinked photosensitizer and reaction products containing the photosensitizer can be followed by the physical property that the photosensitizer absorbs light at a characteristic wavelength and extinction coefficient, so incorporation into products can be monitored by absorbance at that wavelength or a similar wavelength. Linking of one or more photosensitizer molecules to another or to a binder or to a backbone shifts the peak of absorbance in the elution profile in fractions eluted using sizing gel chromatography, e.g., with the appropriate choice of Sephadex G50, G100, or G200 or other such matrices (Pharmacia-Biotech, Piscataway N.J.). Choice of appropriate sizing gel, for example Sephadex gel, can be determined by that gel in which the photosensitizer elutes in a fraction beyond the excluded volume of material too large to interact with the bead, i.e., the uncoupled starting photosensitizer composition interacts to some extent with the fractionation bead and is concomitantly retarded to some extent.

The correct useful gel can be predicted from the molecular weight of the uncoupled photosensitizer. The successful reaction products of photosensitizer compositions coupled to additional moieties generally have characteristic higher molecular weights, causing them to interact with the chromatographic bead to a lesser extent, and thus appear in fractions eluting earlier than fractions containing the uncoupled photosensitizer substrate. Unreacted photosensitizer substrate generally appears in fractions characteristic of the starting material, and the yield from each reaction can thus be assessed both from size of the peak of larger molecular weight material, and the decrease in the peak of characteristic starting material. The area under the peak of the product fractions is converted to the size of the yield using the molar extinction coefficient.

The product can be analyzed using NMR, integrating areas of appropriate product peaks, to determine relative yields with different linkers. A red shift in absorption of a photosensitizer of several nm has often been observed following coupling to a polyamino acid. Linking to a larger moiety such as a protein might produces a comparable shift, as linking to an antibody resulted in a shift of about 3-5 nm in that direction compared to absorption of the free photosensitizer. Relevant absorption maxima and extinction coefficients in 0.1M NaOH/1% SDS are, for chlorin e6, 400 nm and 150,000 $M^{-1}$, $cm^{-1}$, and for benzoporphyrin derivative, 430 nm and 61,000 $M^{-1}$, $cm^{-1}$.

C. Binders

The binder may, without limitation, be a peptide, a cyclic peptide, a polypeptide, a peptidomimetic, a protein, a fusion protein, a hybrid molecule or a dimer, multimer, or a conjugate of the above that binds or quenches, and, thus, may inhibit, suppress, neutralize, or decrease activity of, the photosensitizer. The binder may include, without limitation, a naturally occurring inhibitor, a receptor, a soluble receptor, an antibody, a polyclonal antibody, a monoclonal antibody, a bispecific antibody, an antibody fragment, a single chain antibody, anti-idiotype antibodies, a peptabody, a peptide, an oligopeptides, an oligonucleotide, a cyclic peptide (i.e., a peptide that is circular in nature), a peptide-lipid conjugate, a hormone, an antigen, an epitope, a receptor, a chemokine, a nucleic acid, a ligand or a dimer, multimer, or a conjugate of the above. Naturally occurring binders are binders that quench the photosensitizer and are found in nature.

In one aspect, the binder is a fluorophore. The property that renders a fluorophore (or any other binder) a suitable quencher is the capability of absorbing energy from the activated photosensitizer.

Fluorophores of the present invention can be any known in the art, including photosensitizers, fluorescent dyes, and photoactive dyes.

Photosensitizers can be any known in the art, as previously described. For example, hematoporphyrin derivatives have been used as fluorescent probes to investigate the development of human atherosclerotic plaques (Spokojny (1986) J. Am. Coll. Cardiol. 8:1387-1392). Ideally, the photosensitizer acting as a binder has a different excitation wavelength than the photosensitizer acting to produce a cytotoxic effect on the pathogen or host cell infected with the pathogen.

Fluorescent dyes of the present invention can be any known in the art, including, but not limited to 6-carboxy-4',5'-dichloro-2', 7'-dimethoxyfluorescein succinimidyl ester; 5-(and-6)-carboxyeosin; 5-carboxyfluorescein; 6-carboxyfluorescein; 5-(and-6)-carboxyfluorescein; 5-carboxyfluorescein-bis-(5-carboxymethoxy-2-nitrobenzyl) ether, -alanine-carboxamide, or succinimidyl ester; 5-carboxyfluorescein succinimidyl ester; 6-carboxyfluorescein succinimidyl ester; 5-(and-6)-carboxyfluorescein succinimidyl ester; 5-(4,6-dichlorotriazinyl) aminofluorescein; 2',7'-difluorofluorescein; eosin-5-isothiocyanate; erythrosin-5-isothiocyanate; 6-(fluorescein-5-carboxamido) hexanoic acid or succinimidyl ester; 6-(fluorescein-5-(and-6)-carboxamido) hexanoic acid or succinimidyl ester; fluorescein-5-EX succinimidyl ester; fluorescein-5-isothiocyanate; fluorescein-6-isothiocyanate; Oregon Green® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidyl ester or triethylammonium salt; Oregon Green® 514 carboxylic acid; Oregon Green® 514 carboxylic acid or succinimidyl ester; Rhodamine Green™ carboxylic acid, succinimidyl ester or hydrochloride; Rhodamine Green™ carboxylic acid, trifluoroacetamide or succinimidyl ester; Rhodamine Green™-X succinimidyl ester or hydrochloride; Rhodol Green™ carboxylic acid, N,O-bis-(trifluoroacetyl) or succinimidyl ester; bis-(4-carboxypiperidinyl) sulfonerhodamine or di(succinimidyl ester); 5-(and-6)-carboxynaphthofluorescein, 5-(and-6)-carboxynaphthofluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(and-6)-carboxyrhodamine 6G succinimidyl ester; 5-carboxy-2',4',5',7'-tetrabromosulfonefluorescein succinimidyl ester or bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodamine succinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green isothiocyanate; NANOGOLD® mono(sulfosuccinimidyl ester); QSY® 21 carboxylic acid or succinimidyl ester; QSY® 7 carboxylic acid or succinimidyl ester; Rhodamine Red™-X succinimidyl ester; 6-(tetramethylrhodamine-5-(and-6)-carboxamido)hexanoic acid succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6)-isothiocyanate.

Fluorescent dyes of the present invention can also be, for example, bodipy dyes commercially available from Molecular Probes, including, but not limited to BODIPY® FL; BODIPY® TMR STP ester; BODIPY® TR-X STP ester; BODIPY® 630/650-X STP ester; BODIPY® 650/665-X STP ester; 6-dibromo-4,4-difluoro-5, 7-dimethyl-4-bora-3a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora-3a,4a-diaza-s-indacene-3-pentanoic acid succinimidyl ester; 4,4-difluoro-5,7-dimethyl-4-bora-3a,4a-diaza-s-indacene-3-propionic acid; 4,4-difluoro-5,7-dimethyl-4-bora-3a,4a-diaza-s-indacene-3-propionic acid succinimidyl ester; 4,4-difluoro-5,7-dimethyl-4-bora-3a,4a-diaza-s-indacene-3-propionic acid sulfosuccinimidyl ester or sodium salt; 6-((4, 4-difluoro-5,7-dimethyl-4-bora-3a,4a-diaza-s-indacene-3-propionyl)amino)hexanoic acid; 6-((4,4-difluoro-5,7-dimethyl-4-bora-3a,4a-diaza-s-indacene-3-propionyl) amino)hexanoic acid or succinimidyl ester; N-(4,4-difluoro-5,7-dimethyl-4-bora-3a,4a-diaza-s-indacene-3-propionyl) cysteic acid, succinimidyl ester or triethylammonium salt; 6-4,4-difluoro-1,3-dimethyl-5-(4-methoxyphenyl)-4-bora-3a,4a 4,4-difluoro-5,7-diphenyl-4-bora-3a,4a-diaza-s-indacene-3-propionic acid; 4,4-difluoro-5,7-diphenyl-4-bora-3a,4a-diaza-s-indacene-3-propionic acid succinimidyl ester; 4,4-difluoro-5-phenyl-4-bora-3a,4a-diaza-s-indacene-3-propionic acid succinimidyl ester; 6-((4,4-difluoro-5-phenyl-4-bora-3a,4a-diaza-s-indacene-3-propionyl)amino)hexanoic acid or succinimidyl ester; 4,4-difluoro-5-(4-phenyl-1, 3-butadienyl)-4-bora-3a,4a-diaza-s-indacene-3-propionic acid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yOstyryloxy)acetyl)aminohexanoic acid or succinimidyl ester; 4,4-difluoro-5-styryl-4-bora-3a,4a-diaza-s-indacene-3-propionic acid; 4,4-difluoro-5-styryl-4-bora-3a, 4a-diaza-s-indacene-3-propionic acid succinimidyl ester; 4,4-difluoro-1,3,5,7-tetramethyl-4-bora-3a,4a-diaza-s-indacene-8-propionic acid; 4,4-difluoro-1,3,5,7-tetramethyl-4-bora-3a,4a-diaza-s-indacene-8-propionic acid succinimidyl ester; 4,4-difluoro-5-(2-thienyl)-4-bora-3a,4a-diaza-s-indacene-3-propionic acid succinimidyl ester; 6-(((4-(4,4-difluoro-5-(2-thienyl)-4-bora-3a,4a-diaza s-indacene-3-yl)

phenoxy)acetyl) amino)hexanoic acid or succinimidyl ester; and 6-(((4,4-difluoro-5-(2-thienyl)-4-bora-3a,4a-diaza-s-indacene-3-yl)styryloxy)acetyl)aminohexanoic acid or succinimidyl ester.

Fluorescent dyes the present invention can also be, for example, alexa fluor dyes commercially available from Molecular Probes, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 647 carboxylic acid; Alexa Fluor® 660 carboxylic acid; and Alexa Fluor® 680 carboxylic acid.

Fluorescent dyes the present invention can also be, for example, cy dyes commercially available from Amersham-Pharmacia Biotech, including, but not limited to Cy3 NHS ester; Cy 5 NHS ester; Cy5.5 NHS ester; and Cy 7 NHS ester.

Photoactive dyes of the present invention can be any photosensitizer known in the art which will fluoresce but not necessarily produce a reactive species in phototoxic amounts when illuminated. Depending on the wavelength and power of light administered, a photosensitizer can be activated to fluoresce and, therefore, act as a photoactive dye, but not produce a phototoxic effect unless, in some cases, the wavelength and power of light is suitably adapted to induce a phototoxic effect.

Throughout this specification, any reference to a binder should be construed to refer to each of the binders identified and contemplated herein and to each biologically equivalent molecule. "Biologically equivalent" means compositions of the present invention which are capable of preventing action of the photosensitizer in a similar fashion, but not necessarily to the same degree.

D. Backbones

Pesticidal compositions according to the invention include those in which a "backbone" moiety, such as a polyamino acid, is linked to a photosensitizer and/or to a binder.

Inclusion of a backbone in a composition with a photosensitizer and/or binder can provide a number of advantages, including the provision of greater stoichiometric ranges of photosensitizers and/or binders and/or targeting moieties coupled per backbone. If the backbone possesses intrinsic affinity for a target pest, the affinity of the composition can be enhanced by coupling to the backbone.

Peptides useful in the methods and compounds of the invention for design and characterization of backbone moieties include poly-amino acids which can be homo- and hetero-polymers of L-, D-, racemic DL- or mixed L- and D-amino acid composition, and which can be of defined or random mixed composition and sequence. Examples of naturally-occurring peptides with mixed D and L amino acid residues include bacitracin and tyrocidin. These peptides may be modeled after particular natural peptides, and optimized by the technique of phage display and selection for enhanced binding to a chosen target, so that the selected peptide of highest affinity is characterized and then produced synthetically.

Further modifications of functional groups can be introduced for purposes, for example, of increased solubility, decreased aggregation, and altered extent of hydrophobicity. Examples of non-peptide backbones include nucleic acids and derivatives of nucleic acids such as DNA, RNA and peptide nucleic acids; polysaccharides and derivatives such as starch, pectin, chitins, celluloses and hemi-methylated celluloses; lipids such as triglyceride derivatives and cerebrosides; synthetic polymers such as polyethylene glycols (PEGs) and PEG star polymers; dextran derivatives, polyvinyl alcohols, N-(2-hydroxypropyl)-methacrylamide copolymers, poly (DL-glycolic acid-lactic acid); and compositions containing elements of any of these classes of compounds.

III. Pests and Administration of the Pesticidal Compositions of the Invention

A) Plant and Plant Organs

The pesticidal compositions are suitable for protecting plants and plant organs, for increasing the harvest yields, for improving the quality of the harvested goods and for controlling animal pests, in particular insects, arachnids and nematodes, which are encountered in agriculture, in forests, in gardens and leisure facilities, in the protection of stored products and of materials, and in the hygiene sector, and have good plant tolerance, favorable toxicity to warm-blooded animals and good environmental compatibility. They may preferably be employed as crop protection agents.

In certain embodiments, the pesticidal compositions according to the invention can be used, for example, and without limitation, to treat propagation material such as tubers or rhizomes, but also seeds, seedlings or seedlings pricking out and plants or plants pricking out. These methods of treatment can also be useful to treat roots. The methods of treatment according to the invention can also be useful to treat the overground parts of the plant such as trunks, stems or stalks, leaves, flowers and fruit of the concerned plant.

Plants in accordance with the invention include, but are not limited to corn; tobacco; cotton; soybean; sugarcane; hay; sorghum; kales; cabbages; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantains), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops, including flowers; as well as genetically modified homologues of these crops.

In certain embodiments, the pesticidal compositions according to the invention can be also used, for example, and without limitation, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis,*

*Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.* Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

B) Formulation i) For Use in Plants

The pesticidal compositions of the invention can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The pesticidal compositions of the invention can be applied both before and after emergence of the plants. They can also be incorporated into the soil before sowing.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the pesticidal compositions is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The pesticidal compositions can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the pesticidal compositions with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable Solid Carriers are: for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The pesticidal compositions of the invention can be used in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

ii.) For Household or Industrial Use

In the field of household or industrial use, the pesticidal compositions of the invention are used alone or in combination with other suitable active compounds, such as phosphoric acid esters, carbamates, pyrethroids, neonicotinoides, growth regulators or active compounds from other known classes of pesticides.

The pesticidal compositions of the invention can be used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

iii.) For Antifouling Use

Using the compounds according to the invention as an antifouling agent, alone or in combination with other active compounds, allows the use of heavy metals such as, for example, in bis-(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyndine)-bismuth chloride, tri-n-butyl-tin fluoride, manganese ethylenebisthio-carbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

The pesticidal compositions can be used to control fouling by mixing the compositions into ready-to-use antifouling paints If appropriate, the ready-to-use antifouling paints can additionally comprise other active compounds, preferably algicides, fungicides, herbicides, molluscicides, or other antifouling active compounds.

The antifouling compositions used comprise the active compound according to the invention of the compounds according to the invention in a concentration of 0.001 to 50% by weight, in particular 0.01 to 20% by weight. Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Antifouling paints can further comprise, in particular, binders. Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

iv.) For Veterinary Use

In the field of veterinary uses, the pesticidal compositions of the invention can be used in a known manner by enteral administration in the form of, for example, tablets, capsules, portions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

v.) For Use in Humans

In humans, a therapeutically effective amount of a composition of the invention can be administered in one or more doses. An effective amount is an amount that is sufficient to palliate, ameliorate, reduce, stabilize, reverse or slow the progression of a pest infestation, such as a parasite infestation, or tick infestation. A therapeutically effective amount can be provided in one or a series of administrations. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the form of the nanoparticle being administered.

Compositions of the present invention may be administered by a mode appropriate for the form of composition. Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with nanoparticle compositions. Therapeutic nanoparticle compositions (e.g., a nanoparticle containing a photosensitizer core, a polymer shell, and a targeting aptamer fixed to the surface of the shell in an appropriate excipient) are often administered by injection or by gradual perfusion.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, compositions are preferably supplied in unit dosage form suitable for administration of a precise amount. Also contemplated by this invention are slow release or sustained release forms, whereby a relatively consistent level of the active compound are provided over an extended period.

Another method of administration is intralesionally, for instance by direct injection directly into the site of pest infestation. Intralesional administration of various forms are useful in that they do not cause the toxicity seen with systemic administration of immunologic agents (Fletcher and Goldstein, 1987), (Rabinowich et al., 1987), (Rosenberg et al., 1986), (Pizza et al., 1984).

C) Pests i. Plant Pests

The pesticidal compositions are active against normally sensitive and resistant species and against all or some stages of development. The abovementioned pests include, but are not limited to:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

ii. Phytoparasitic Nematodes

The pesticidal compositions of the invention are active act against phytoparasitic nematodes including, but are not limited to: *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

iii. Veterinary and Livestock Pests

The pesticidal compositions of the invention are also useful in the veterinary medicine sector against animal parasites (ectoparasites), such as hard ticks, soft ticks, mange mites, harvest mites, flies (biting and licking), parasitic fly larvae, lice, hair lice, feather lice and fleas. These parasites include, but are not limited to:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and Panstrongylus spp.

From the order of the Blattarida, for example *Blatta orientalis, Periplaneta americana, Blattela germanica* and *Supella* spp.

From the subclass of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyle-* tiella spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions of the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

iv. Industrial Pests

The pesticidal compositions of the invention are also useful against insects which destroy industrial materials.

These pests include, but are not limited to:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*.

Hymenopterons, such as *Sirex juvencus, Urocerus gigas, Urocerus gigas taignus, Urocerus augur*.

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*. Bristletails, such as *Lepisma saccharina*.

Industrial materials in the present connection are to be understood as meaning non-living materials, such as, preferably, plastics, adhesives, sizes, paper and card, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

v. Enclosed Spaces/Household Pests

The pesticidal compositions of the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic pesticide products for controlling these pests. They are active against sensitive and resistant species and against all developmental stages. These pests include, but are not limited to:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

vi. Parasites of Animal and Human.

The pesticidal compositions of the invention are also suitable for controlling parasites which can infest animals and humans. They can be employed alone or in combination with other active compounds for controlling these pests and symptoms related to the infestation of such pests. They are active against sensitive and resistant species and against all developmental stages. These pests include, but are not limited to ticks, lice, mites, strongyles, nematode parasites, such as ascarids (*Ascaris*) (including *Ascaris lumbricoides* (Large Roundworm of Man)), filarias, hookworms, pinworms (including *Enterobius vermicularis*—(The Human Pinworm)) whipworms (*Trichuris trichiura*), *Trichinella spiralis*, *Dirofilaria immitis* (heartworms), *Haemonchus contortus*, and *Myrmeconema neotropicum*.

vii. Fouling Pests

The pesticidal compositions of the invention are also suitable for controlling pests which cause fouling of ships and other objects which come into contact with saltwater or brackish water, such as hulls, screens, nets, buildings, moorings and signalling systems, against fouling.

Such fouling includes, but is not limited to, fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

viii. Pests Expressing β-Lacatamase

The invention is based, at least in part, on the discovery that when a pest, e.g., an arthopod, a nematode, an insect, or a parasite, ingests an enzyme-cleavable ß-lactamase specific construct, the construct is cleaved by ß-lactamases that are produced by the pest, resulting in the release of free photosensitizer within the insect. The pest then dies when exposed to light. In accordance with the invention, the pest is an animal that expresses ß-lactamase. In particular embodiments, In accordance with the invention, the pest is an animal that expresses a ß-lactamase comprising the protein domain sequence:

(SEQ ID NO: 1)
ILTEKRKILVDCGDPWNGTQIIQALSKYSLNCDDITDLIITHGHSDHCGN

LSLFQQAKIYMGDDMAKDGIYEGIWTLDDFVKIRPTPGHTDRSIIVLDTE

YGTVAIVGDIFEEENDDDSWKENSKYPEEQQKSRKIILKEADWIIPGH (GenBANK protein sequence XP_001891895), or a fragment thereof.

In certain embodiments, the pest expresses a ß-lactamase comprising a protein domain of at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, identity (e.g., when compared to the overall length of the protein sequence) to SEQ ID NO:1 or a fragment thereof.

In still other embodiments, the pest is an animal that expresses a ß-lactamase comprising the protein domain sequence:

(SEQ ID NO: 2)
TNTYIIGTGKRRILLDAGDENVPEYIGHLKKVISDERILINDIIVSHWHH

DHIGGVDEVLDIIENKDSCKVWKFPRADAPDGTIRNANINHLKHGQKFNI

EGATLEVLHTPGHTTDHVVLVLHEDNSLFSADCILGEGSTVFEDLYEYTK

SLQAIQDAKPSVIYPG (GenBANK protein sequence

XP_001656361)

or a fragment thereof.

In certain embodiments, the pest expresses a ß-lactamase comprising a protein domain of at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, identity (e.g., when compared to the overall length of the protein sequence) to SEQ ID NO:2 or a fragment thereof.

To determine the percent identity or similarity of two protein domain sequences, the sequences are aligned for optimal comparison purposes (e.g., gaps can be introduced in the sequence of a first protein sequence for optimal alignment with a second protein sequence). As used herein, the terms "percent identity" and "percent similarity" are used interchangeably.

When a position in the first sequence is occupied by the same amino acid residue as the corresponding position in the second sequence, then the molecules are similar at that position. The percent similarity between the two sequences is a function of the number of similar positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) *Nucleic Acids Research* 25(17): 3389-3402. When utilizing BLAST and Gapped BLAST programs, the default parameters of the respective programs (e.g., XBLAST and NBLAST) can be used. See http://www.ncbi.nlm.nih.gov. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

Alternatively, the percent identity between two protein sequences can be determined using the GAP program in the GCG software package, using either a Blossom 62 matrix or a PAM250 matrix, and a gap weight of 12, 10, 8, 6, or 4 and a length weight of 2, 3, or 4.

In other embodiments, percent identity is determined at the polynucleotide level. A ß-lactamase polynucleotide is one that encodes a ß-lactamase polypeptide. In particular embodiments, a polynucleotide encoding a ß-lactamase polypeptide are identified by hybridizing the polynucleotide sequence with a ß-lactamase probe. Hybridization conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A particular, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A particular, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A particular, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M).

It will also be recognized by the skilled practitioner that additional reagents can be added to hybridization and/or wash buffers to decrease non-specific hybridization to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or, alternatively, 0.2×SSC, 1% SDS).

vii. Combinations

The pesticidal compositions of the invention can be used as a mixture with other known active compounds, such as additional pesticide materials, fungicides, insecticides, acaricides, nematicides, bird repellents, plant nutrients and agents which improve soil structure, is also possible. The pesticidal composition of the present invention may include attractants such as cockroach pheromones (e.g., sex attractants, aggregation pheromones) or food-based attractants (e.g., methylcyclopentenalone, maltol, fenugreek and other flavorings).

For example, and without limitation, the pesticidal compositions of the invention can be used as a mixture with known acaricides, nematicides or insecticides.

Suitable Insecticides/Acaricides/Nematicides include, but are not limited to, the following compounds:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluoron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, dinetofuran, diofenolan, disulfoton, docusat-sodium, dofenapyn, eflusilanate, emamectin, empenthrin, endosulfan, Entomopfthora spp., esfenvalerate, ethiofencarb, ethion, ethiprole, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenthion, fenvalerate, fipronil, fluazinam, fluazuron, flubrocythrinate, flucycloxuron, flucythrinate, flufenoxuron, flumethrin, flupyrazofos, flutenzine, fluvalinate, fonophos, fosmethilan, fosthiazate, fubenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, Metharhizium anisopliae, metharhizium flavoviride, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M, *Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI 5302, zeta-cypermethrin, zolaprofos, (1R-cis)-[5-(phenylmethyl)-3-furanyl]-methyl-3-Rdihydro-2-oxo-3 (2H)-furan-ylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,-3, 5-triazine-2(1H)-imine, 2-(2-chloro-6-fluorophenyl)-4-[4-(1,1-dimethylethyl)phenyl]-4,5-dihydro-o-xazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxybenzene, 4-chloro-2-(1,1-dimethylethyl)-5-[[2-(2,6-dimethyl-4-phenoxyphenoxy)ethyl-]thio]-3(2H)-pyridazinone, 4-chloro-2-(2-chloro-2-methylpropyl)-5-[(6-iodo-3-pyridinyl)methoxy]-3(2H-)-pyridazinone, 4-chloro-5-[(6-chloro-3-pyridinyl)methoxy]-2-(3,4-dichlorophenyl)-3(2H)-pyridazinone, *Bacillus thuringiensis* strain EG-2348, [2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate, [3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4, 5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, [0295] N-methyl-N'-2-propenyl-1,2-hydrazinedicarbothioamide, O,O-diethyl-[2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridin-2-yloxy)-propoxy]-benzene.

It is also possible to admix the pesticidal compositions of the invention with other known active compounds, such as herbicides, fertilizers and growth regulators, or safeners or semiochemicals.

IV. Photoactivation

Typically, administration of a pesticidal composition according to the invention is followed by a sufficient period of time to allow accumulation thereof in the pest. The ß-lactamase cleavage site of the linker is cleaved by ß-lactamase produced by the pest. As a result, the photosensitizers are no longer quenched. The photosensitizers can, subsequently, be activated by irradiation. This is accomplished by applying light of a suitable wavelength and intensity, for an effective length of time, so as to kill the pest. As used herein, "irradiation" refers to the use of light to induced a chemical reaction of a photosensitizer.

Photoactivating dosages depend on various factors, including the amount of the pesticide administered, the wavelength of the photoactivating light, the intensity of the photoactivating light, and the duration of illumination by the photoactivating light. Thus, the dose can be adjusted to a therapeutically effective dose by adjusting one or more of these factors. Such adjustments are within the level of ordinary skill in the art.

Irradiation of the appropriate wavelength for a given compound may be administered by a variety of methods. Methods for irradiation include, but are not limited to, the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments that provide transillumination. Delivery of the light to a recessed, or otherwise inaccessible physiological location can be facilitated by flexible fiber optics (implicit in this statement is the idea that one can irradiate either a broad field, such as the lung or a lobe of the lung, or a narrow field where bacterial cells may have localized). The source of the light needed to inactivate the pest can be an inexpensive diode laser or a non-coherent light source.

The photosensitizer compositions of the invention should be stable during the course of at least a single round of treatment by continued or pulsed irradiation, during which the photosensitizer within the composition would, preferably, be repeatedly excited to the energized state, undergoing multiple rounds of generation of singlet oxygen.

The suitable wavelength, or range of wavelengths, will depend on the particular photosensitizer(s) used, and can range from about 350 nm to about 550 nm, from about 550 nm to about 650 nm, from about 650 nm to about 750 nm, from about 750 nm to about 850 nm and from about 850 nm to about 950 nm.

In specific embodiments, pests are illuminated with red light. Given that red and/or near infrared light best penetrates animal tissues, photosensitizers with strong absorbances in the range of about 600 nm to about 900 nm are optimal for PDT. For photoactivation, the wavelength of light is matched to the electronic absorption spectrum of the photosensitizer so that the photosensitizer absorbs photons and the desired photochemistry can occur. Wavelength specificity for photoactivation generally depends on the molecular structure of the photosensitizer. Photoactivation can also occur with sub-ablative light doses. Determination of suitable wavelength, light intensity, and duration of illumination is within ordinary skill in the art.

In a particular embodiment, the pest are illuminated with sunlight (i.e. solar radiation). Such exposure can be direct, indirect, focussed or diffused.

The effective penetration depth, $\delta_{eff}$, of a given wavelength of light is a function of the optical properties of the tissue, such as absorption and scatter. The fluence (light dose) in a tissue is related to the depth, d, as: $e^{-d}/\delta_{eff}$. Typically, the effective penetration depth is about 2 to 3 mm at 630 nm and increases to about 5 to 6 nm at longer wavelengths (about 700 to about 800 nm) (Svaasand and Ellingsen, (1983) Photochem Photobiol. 38:293-299). Altering the biologic interactions and physical characteristics of the photosensitizer can alter these values. In general, photosensitizers with longer absorbing wavelengths and higher molar absorption coefficients at these wavelengths are more effective photodynamic agents.

The light for photoactivation can be produced and delivered to the site of infestation by any suitable means known in the art. Photoactivating light can be delivered to the site of infestation from a light source, such as a laser or optical fiber. Preferably, optical fiber devices that directly illuminate the site of infestation deliver the photoactivating light. For example, the light can be delivered by optical fibers threaded through small gauge hypodermic needles. Light can be delivered by an appropriate intravascular catheter, such as those described in U.S. Pat. Nos. 6,246,901 and 6,096,289, which can contain an optical fiber. Optical fibers can also be passed through arthroscopes. In addition, light can be transmitted by percutaneous instrumentation using optical fibers or cannulated waveguides. For open surgical sites, suitable light sources include broadband conventional light sources, broad arrays of light-emitting diodes (LEDs), and defocused laser beams.

Delivery can be by all methods known in the art, including transillumination. Some photosensitizers can be activated by near infrared light, which penetrates more deeply into biological tissue than other wavelengths. Thus, near infrared light is advantageous for transillumination. Transillumination can be performed using a variety of devices. The devices can utilize laser or non-laser sources, (e.g., lightboxes or convergent light beams).

Where pesticidal activity is desired, the dosage of pesticidal composition, and light activating the photosensitizer composition, is administered in an amount sufficient to produce a phototoxic species effective to kill the pest Irradiation of the appropriate wavelength for a given compound may be administered by a variety of wavelengths. Methods for irradiation include, but are not limited to, the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments that provide transillumination.

The wavelength and power of light can be adjusted according to standard methods known in the art to control the production of phototoxic species. Thus, under certain conditions (e.g., low power, low fluence rate, shorter wavelength of light or some combination thereof), a fluorescent species is primarily produced from the photosensitizer and any reactive species produced has a negligible effect. These conditions are easily adapted to bring about the production of a phototoxic species. For example, where the photosensitizer is chlorin$_{e6}$, the light dose administered to produce a fluorescent species and an insubstantial reactive species is less than about 10 J/cm, preferably less than about 5 J/cm and more preferably less than about 1 J/cm. Determination of suitable wavelength, light intensity, and duration of illumination for any photosensitizer is within the level of ordinary skill in the art.

V. Detection of Pests

In certain embodiments, the administration of the compositions of the invention, followed by photoactivation, does not kill the pest but instead results in the pest fluorescing. As such, in certain embodiments, the invention provides a method for detecting the presence of pests, the method comprising the steps of: contacting the pest with a photosensitizer composition of the invention; cleaving one or more moieties cleavable by αß-lactamase expressed by the pest to dequench the photosensitizer composition, light-activating the composition to produce a fluorescent species, thereby causing the pest to fluoresce and observing the fluorescence thereby detecting the presence of pests.

In still other embodiments, the administration of the pesticidal compositions of the invention, followed by photoactivation, results in both the termination of the pest and the pest fluorescing. As such, in certain embodiments, the invention provides a method of eliminating and detecting a pest, the method comprising the steps of: contacting the pest with a photosensitizer composition of the invention; cleaving one or more moieties cleavable by the ß-lactamase to dequench the photosensitizer composition and light-activating the composition to produce a fluorescent, phototoxic species, thereby eliminating the pest and causing the pest to fluoresce and observing the fluorescence thereby also detecting the presence of the pest.

The invention is additionally described by way of the following illustrative, non-limiting Examples that provide a better understanding of the present invention and of its many advantages.

EXAMPLES

Example 1

Preparation of Conjugates Comprising Polymer, β-lactam Moiety and Photosensitizer In one approach, the synthesis of the conjugates is based on cephalosporin, the most often used β-lactam. It is conceivable to develop penem or carbapenem derivatives subsequently.

In the following, the photosensitizer (a porphyrin molecule with at least one propionic side chain) is represented by PS—CH$_2$—CH$_2$—COOH. The polymer used in the synthetic routes shown below is a linear or branched poly (ethylene glycol) with propionic acid groups (PEG-CH$_2$—CH$_2$—COOH) (Senter, P. D., et al. (1995) Bioconjug. Chem. 6:389-394). However, the chemistry is applicable to similar polymeric materials containing available carboxylic side chains. In order to be released upon enzymatic hydrolysis, the porphyrin molecule is preferably linked at the 3'-position of the cephalosporin. The cephalosporin-porphyrin moiety obtained can then be conjugated to the polymer using the amino group on the β-lactam ring.

The preparation of three different conjugates is proposed, where the porphyrin and cephalosporin are linked via an ester:

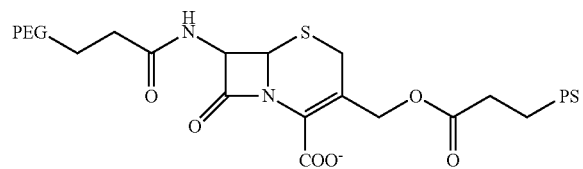

or via a carbamate group:

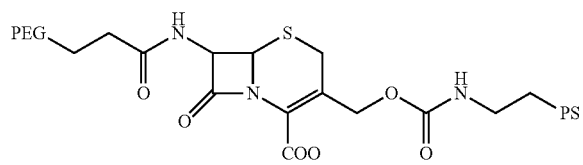

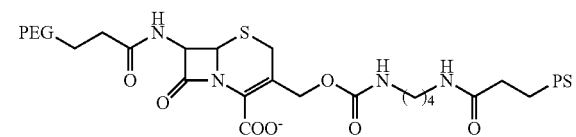

The preparation of a cephalosporin-prophyrin ester comprises the following steps:

A. Protection of the Amino-Group in the β-Lactam Ring

There are several ways to protect the amino group. One is represented below (Hanessian, S., et al. (1993) Can. J. Chem. 71:896-906):

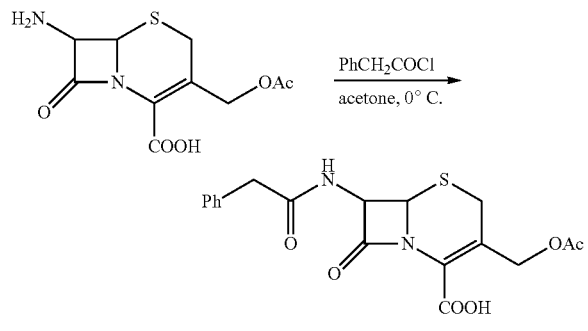

Protected cephalosporin derivatives are commercially available. Other protecting groups include (Albrecht, H. A., et al., (1990) J. Med. Chem. 33:77-86; Albrecht, H. A., et al. (1991) J. Med. Chem. 34:2857-2864; Alexander, R. P., et al. (1991) Tetrahedron Lett. 32:3269-3272):

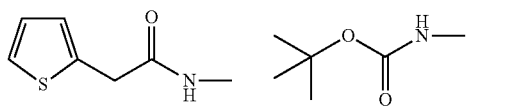

For example, the following molecule (which comes with a protected amino group) is called cephalothin.

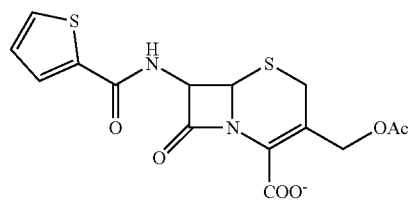

B. Binding of the Porphyrin at the 3'-Position of the Cephalosporin Via an Ester Function
  i. Through a diazomethyl intermediate (Mobashery, S., et al. (1986) J. Biol. Chem. 261:7879-7887)

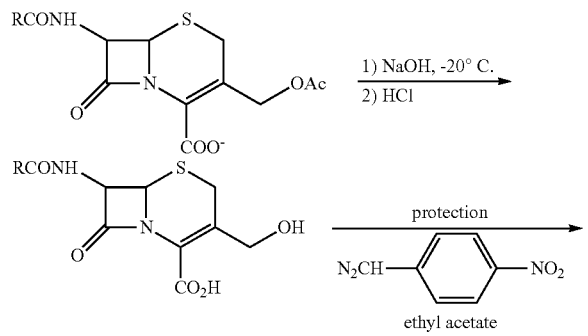

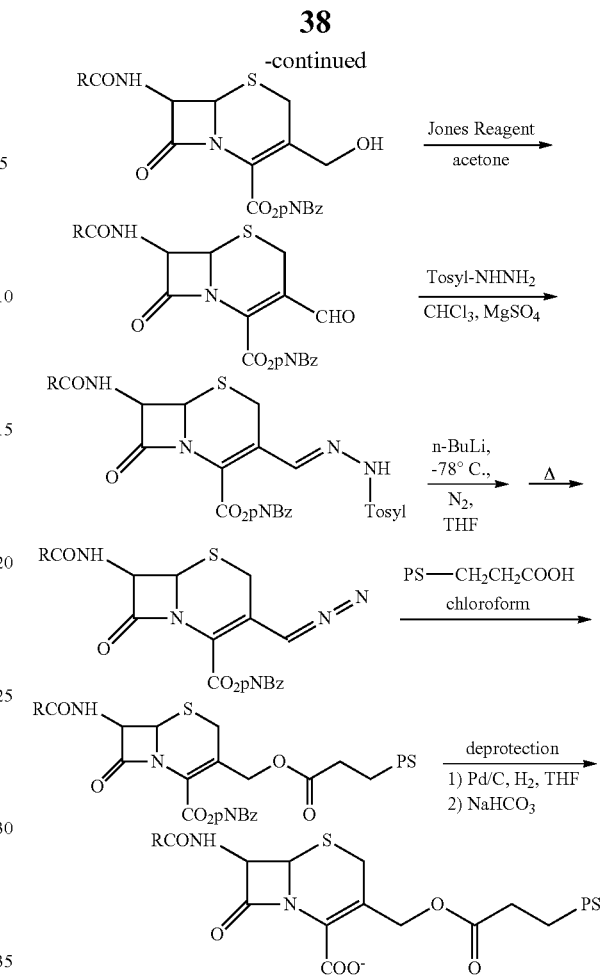

In this scheme, pNBz=para-nitro-benzyl.
  ii. Through a halogenated intermediate (Mobashery, S., et al. (1986) J. Biol. Chem. 261:7879-7887)

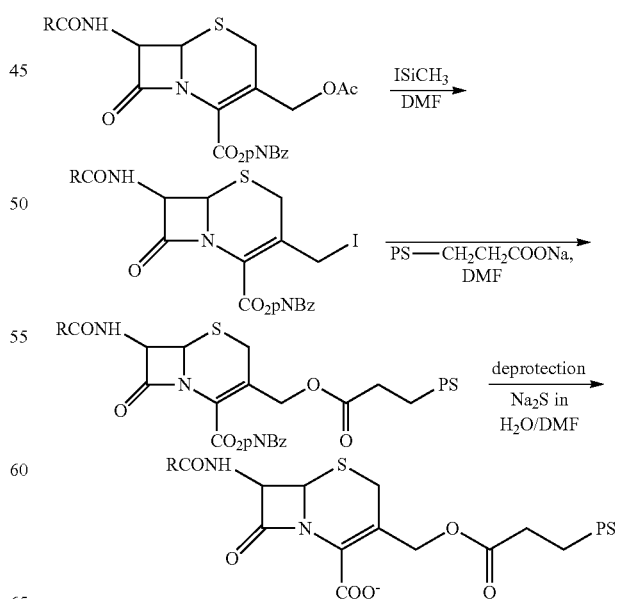

iii. Through a hydroxymethyl intermediate (Hanessian, S., et al. (1993) Can. J. Chem. 71:896-906)

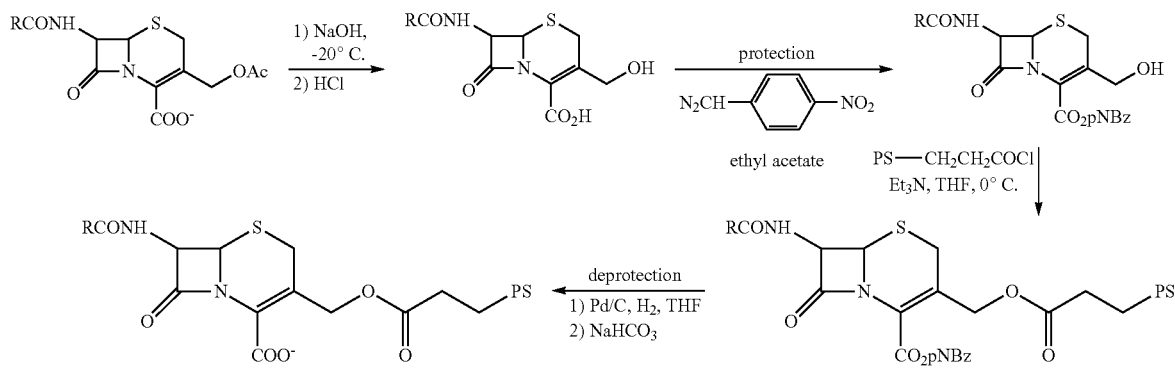

C. Deprotection of the Amino-Group in the B-Lactam Ring (Albrecht, H. A., et al. (1991) J. Med. Chem. 34:669-675)

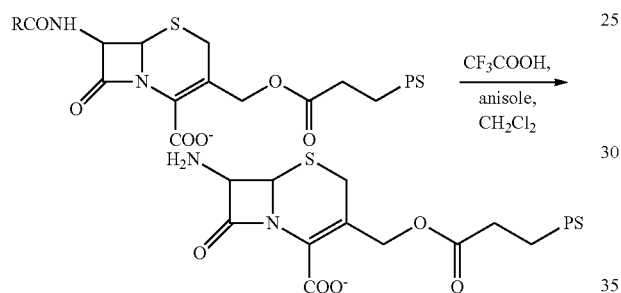

Deprotection of the amino group is also very often carried out using Penicillin-G amidase (PGA) (Vrudhula, V. M., et al. (1995) J. Med. Chem. 38:1380-1385).

D. Conjugation of the Cephalosporin-Porphyrin Moiety to a Polymer (Senter, P. D., et al. (1995) Bioconjug. Chem. 6:389-394)

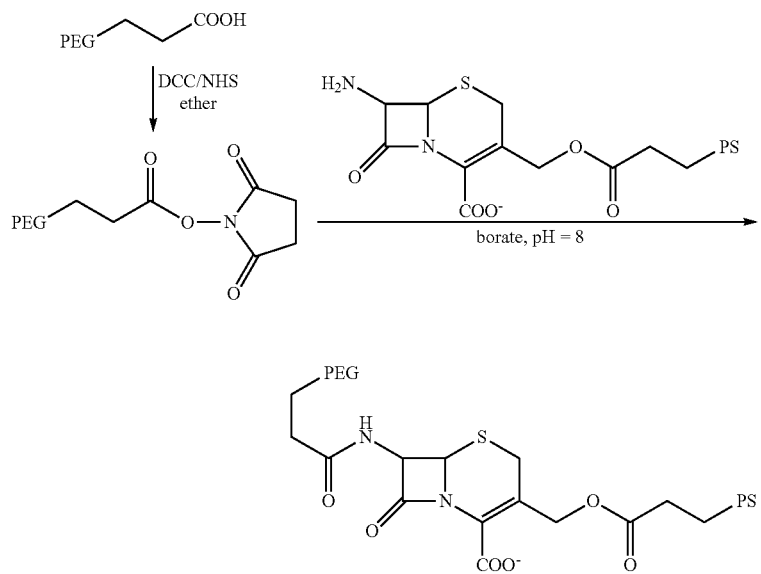

The preparation of a cephalosporin-porphyrin carbamate comprises the following steps:

A. Protection of the amino-group in the β-lactam ring (see above)

B. Binding of the porphyrin at the 3'-position of the cephalosporin via a carbamate i. Direct coupling between the porphyrin and cephalosporin (Alexander, R. P., et al. (1991) Tetrahedron Lett. 32:3269-3272; Rodrigues, M. L., et al. (1995) Chem. & Biol. 2:223-227; Smith, K. M., et al. (1987) Heterocycles 26:1947-1963)

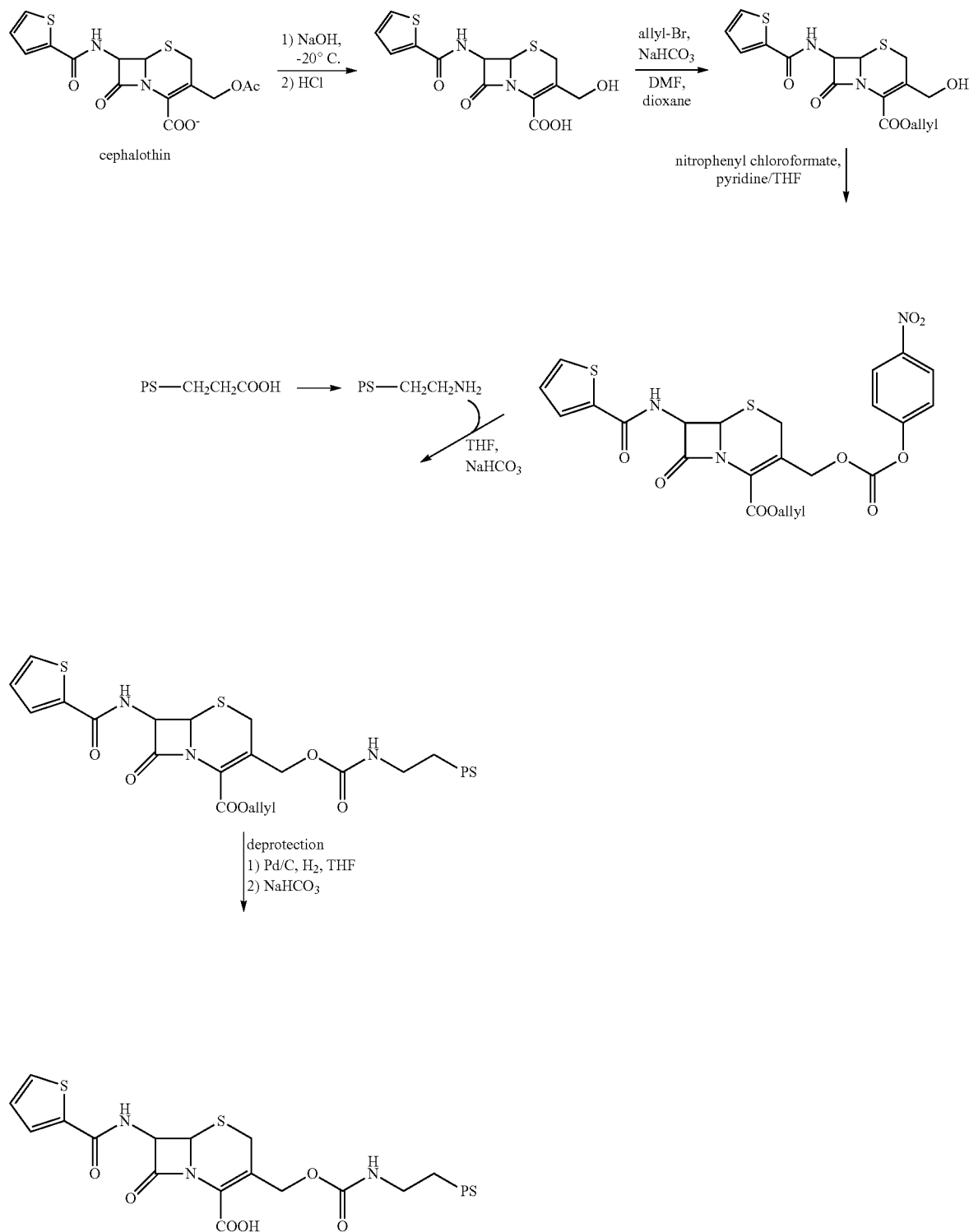

ii. Coupling through a linker (Alexander, R. P., et al. (1991) Tetrahedron Lett. 32:3269-3272; Rodrigues, M. L., et al. (1995) Chem. & Biol. 2:223-227; Boutorine, A. S., et al. (1996) J. Am. Chem. Soc. 118:9469-9476)

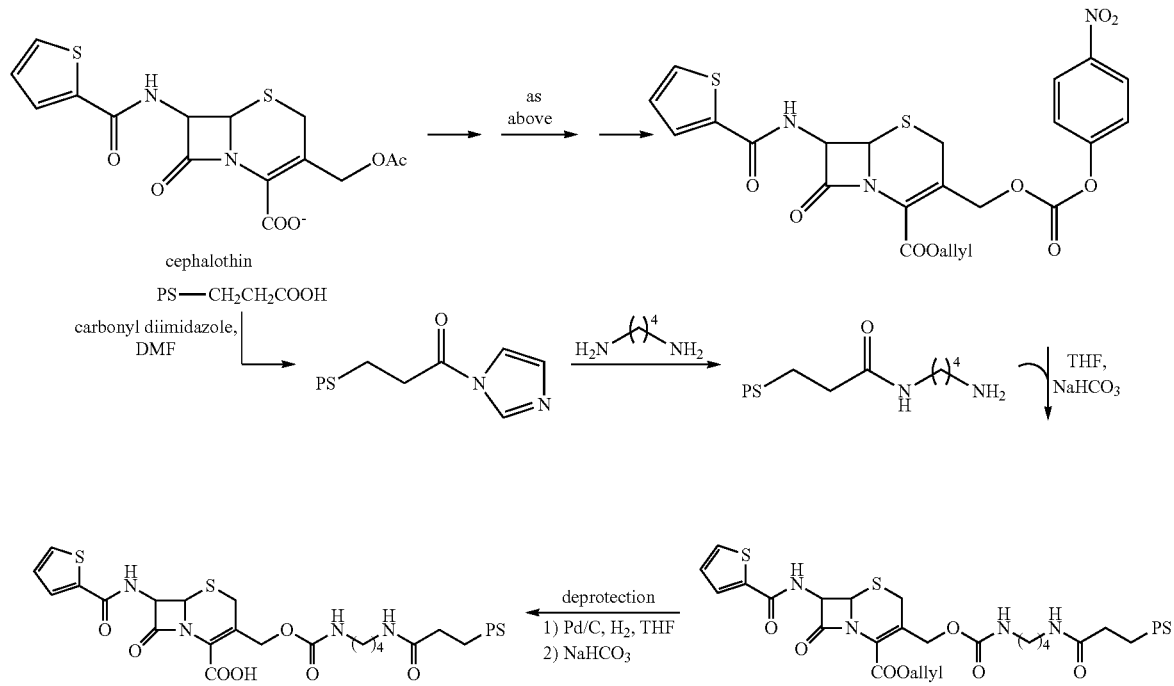

C. Deprotection of the amino-group in the β-lacatam ring (see above)

D. Conjugation of the cephalosporin-porphyrin moiety to a polymer (Senter, P. D., et al. (1995) Bioconjug. Chem. 6:389-394) (see above)

Of additional note, if, after these chemical modifications, the cephalosporin derivatives described above retain their properties as substrates for β-lactamases, one can expect to observe the enzyme-dependent release of three different porphyrin moieties:

PS-Ch$_2$-CH$_3$:

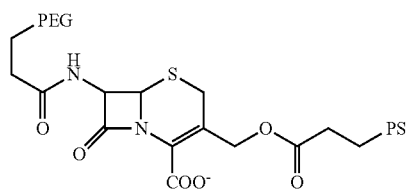

-continued

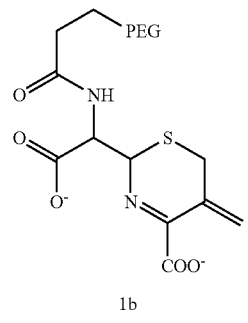

PS—CH$_2$—CH$_2$—NH$_2$:

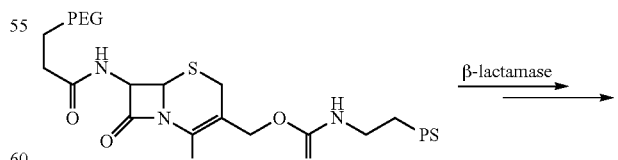

and PS—CH$_2$—CH$_2$—CO—NH—(CH$_2$)$_4$—NH$_2$:

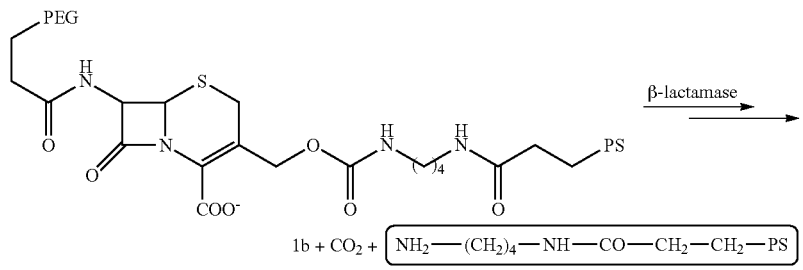
Example 2
Development of Carbamate-Linked Photosensitizer, Inactive (with or without Light) while Linked and Light-Activatable Only when Released by the β-Lactamase Enzyme-Mediated Cleavage
The lactam ring opening of the prodrugs releases the photosensitizer and make it light-activatable for photokilling (FIG. 1).
Synthesis
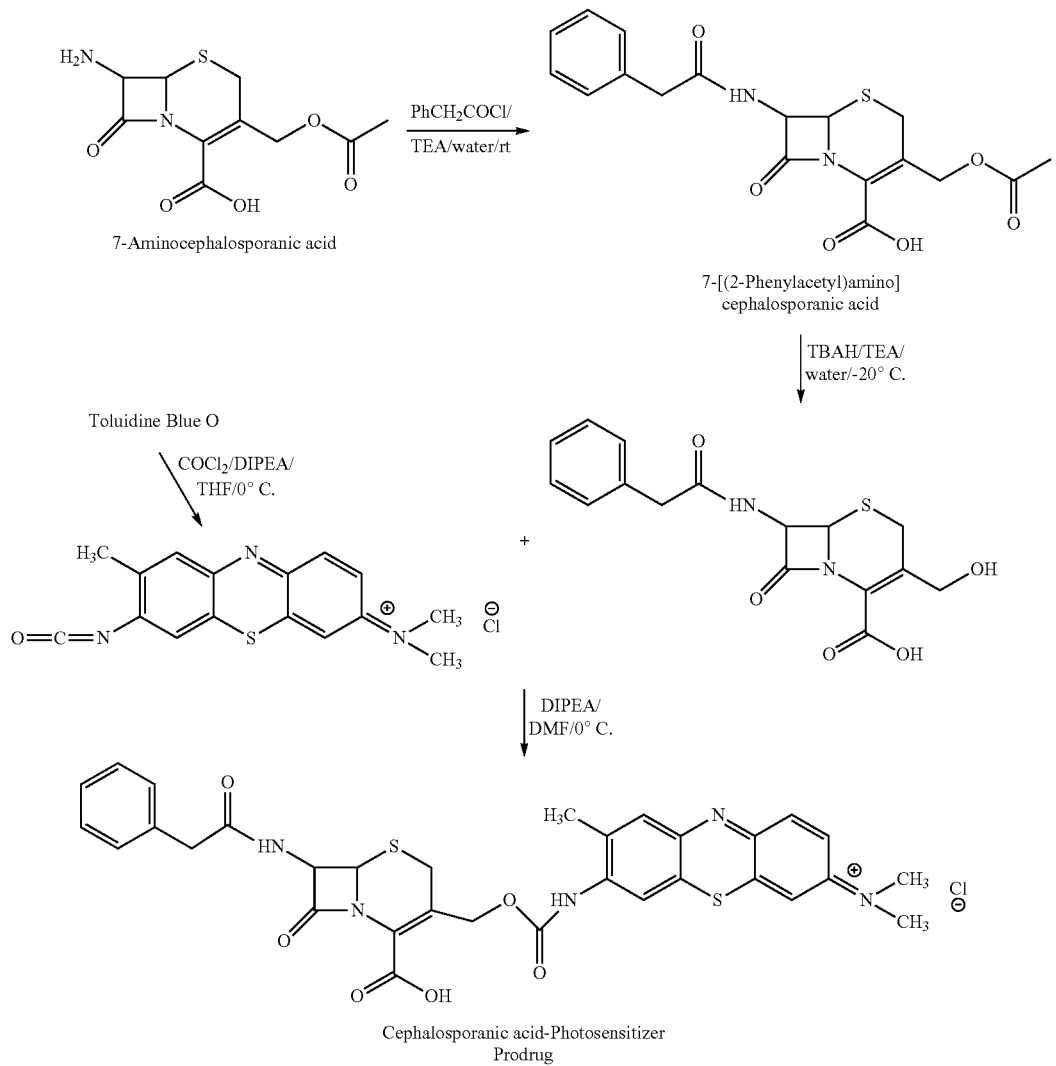

Commercially available 7-aminochephalosporanic acid was reacted with phenylacetyl chloride under Shotten-Baumann reaction conditions to achieve an amino protected chephalosporin molecule. This was further de-esterified using tetrabutylammonium hydroxide as a base to yield easily functionalizable hydroxy end group on cephalosporin. The last step of the synthesis was achieved in a one-pot reaction sequence. Toluidine Blue O (TBO) was converted into its isocynate derivative in the presence of diphosgene. The carbamate-linked prodrug was obtained by adding Cephalosporin derivative to the same reaction mixture.

Synthesis of 7-[(2-phenylacetyl)amino] Cephalosporanic Acid

To a stirred mixture of sodium bicarbonate (2.1 g, 25 mmol) in water (40 ml) and acetone (30 ml), added 7-(phenylacetyl)amino cephalosporanic acid. Stirred this solution for nearly 15 min in ice bath and slowly added phenylacetyl chloride (2.5 ml, 20 mmol) over the period of 30 min. This reaction mixture was stirred overnight and acidified to pH 2.0 with 1N hydrochloric acid. Precipitates obtained were extracted with dichloromethane and washed with water. Dried over magnesium sulphate and solvent evaporated to give off-white solid. The solid sample was stirred overnight in diethyl ether and filters to obtain crude product in 80% yield.

Synthesis of 7-[(2-phenylacetyl)amino] 3-hydrodxymethy Cephalosporanic Acid

To a suspension of 7-[(2-phenylacetyl)amino] cephalosporanic acid (0.5 g, 1.28 mmol) in a a mixture of methane (4 ml) and water (2.5 ml), triethylamine (0.21 ml, 1.54 mmol) was added in 15 min at 0-5° C. To this solution, tetrabutylammonium hydroxide (30% solution in water, 1.53 g, 1.92 mmol) was added at −18° C. in 30 minutes. The reaction mixture was maintained at −18° C. for nearly 7.0 h and acidified to pH 5.0 using glacial acetic acid. Purification was done using C-18 reverse phase column and pure product was obtained as white solid in 67% yield.

Synthesis of Cephalosporanic Acid-Toluidine blueO Prodrug

To a magnetically stirred suspension of toludine blue O (0.1 g, 0.33 mmol) in anhydrous THF (3 ml) under nitrogen was added a solution of tricholoromethyl chloroformate (19.7 μl, 0.164 mmol) over activated charcoal as a catalyst. The reaction mixture was stirred at 55° C. for 30 min. Progress of reaction was monitored using mass spectroscopy for formation of isocynate derivative of toludine blue O. Cooled the flask to room temperature and added a solution of 7[(2-phenylacetyl)amino] 3-hydrodxymethy cephalosporanic acid (0.15 g, 0.33 mmol) in anhydrous dichloromethane (1 ml). The reaction flask was cooled to 0° C. and slowly added diisopropylethylamine (57.0 μl, 0.33 mmol). Stirred for 3.0 h and purified using C18 column with acetonirile and water as eluting solvents. Pure product obtained as a blue solid in 25% yield.

Figure 2A:
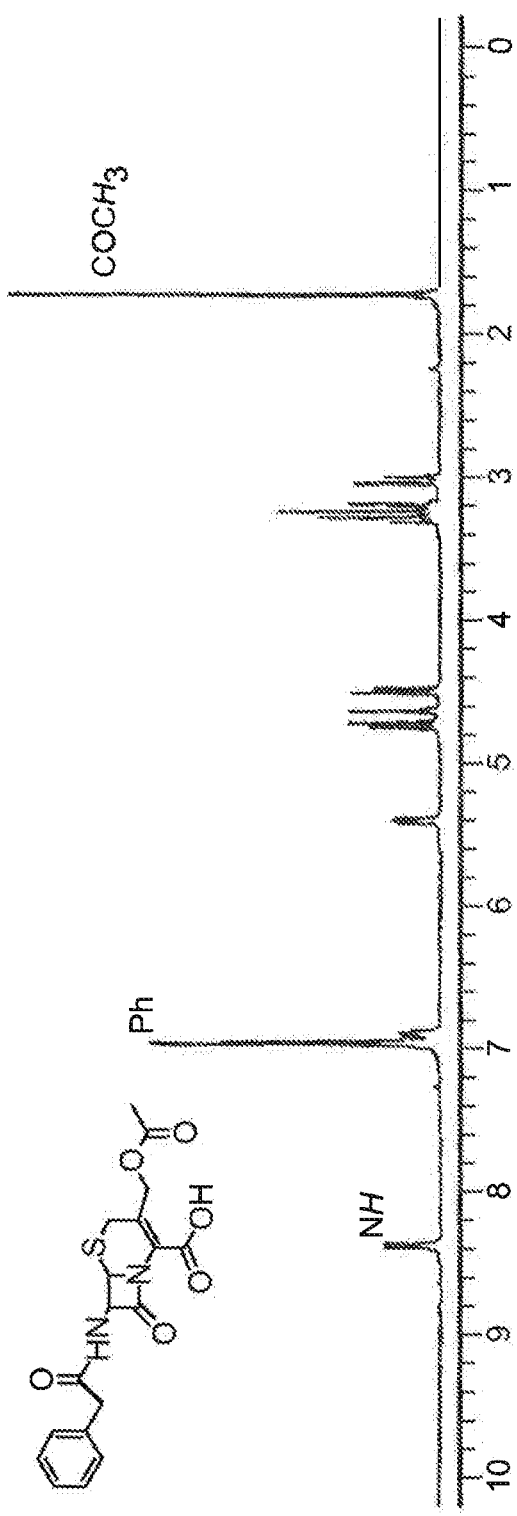
FIG. 2A shows $^1$H NMR spectra obtained for 7-[(2-phenylacetyl)amino] cephalosporanic acid in $CDCl_3$ as a solvent.
Figure 2B:
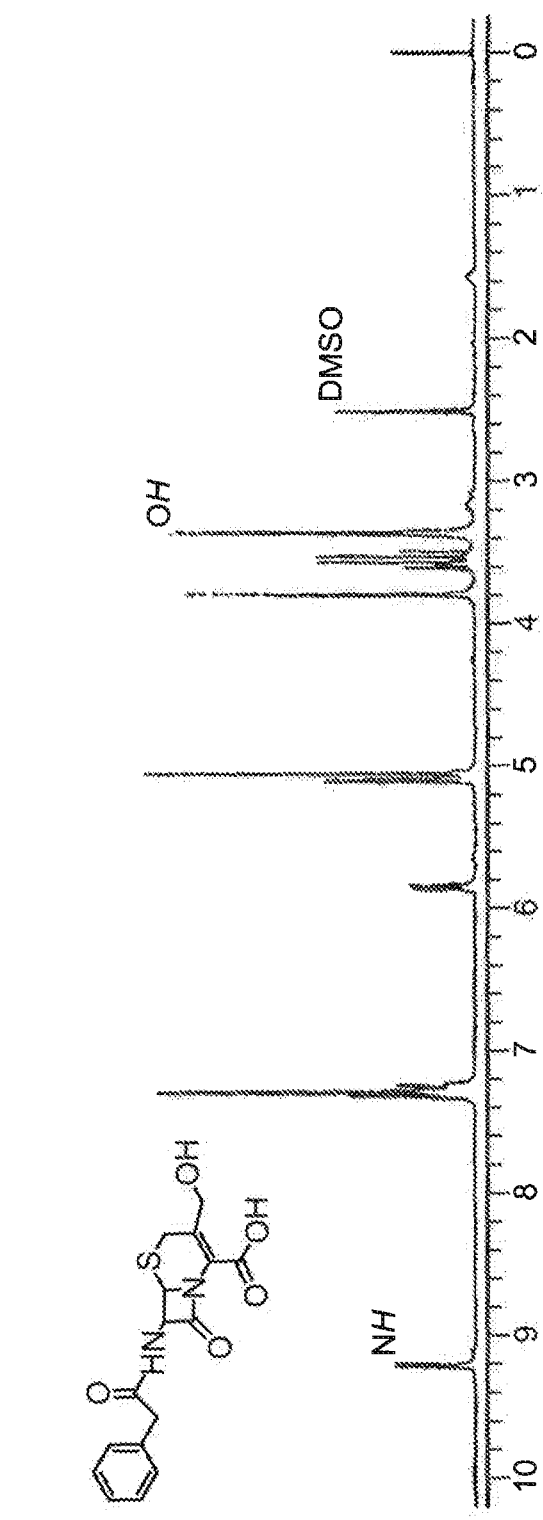
FIG. 2B shows $^1$H NMR spectrum obtained for 7-[(2-phenylacetyl)amino] 3-hydrodxymethy cephalosporanic acid in $DMSO-d_6$ as a solvent. Major proton peaks are marked on the spectra.
Figure 3A:
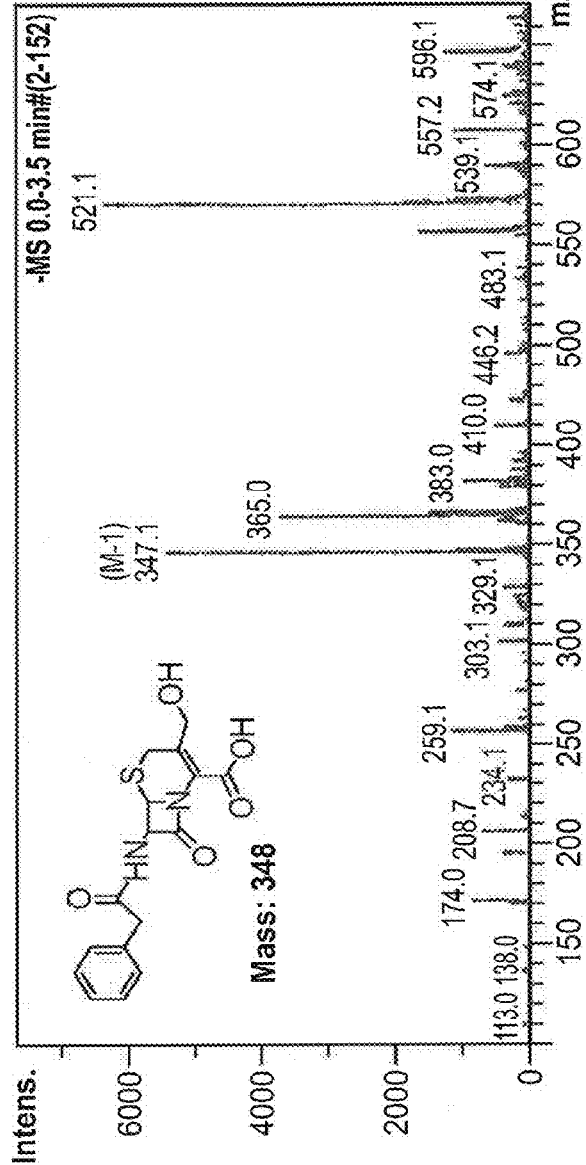
FIGS. 3A and B show MS spectra obtained for (a) 7-[(2-phenylacetyl)amino] 3-hydrodxymethy cephalosporanic acid; and (b) cephalosporanic acid-toluidine blue O prodrug.
Figure 3B:
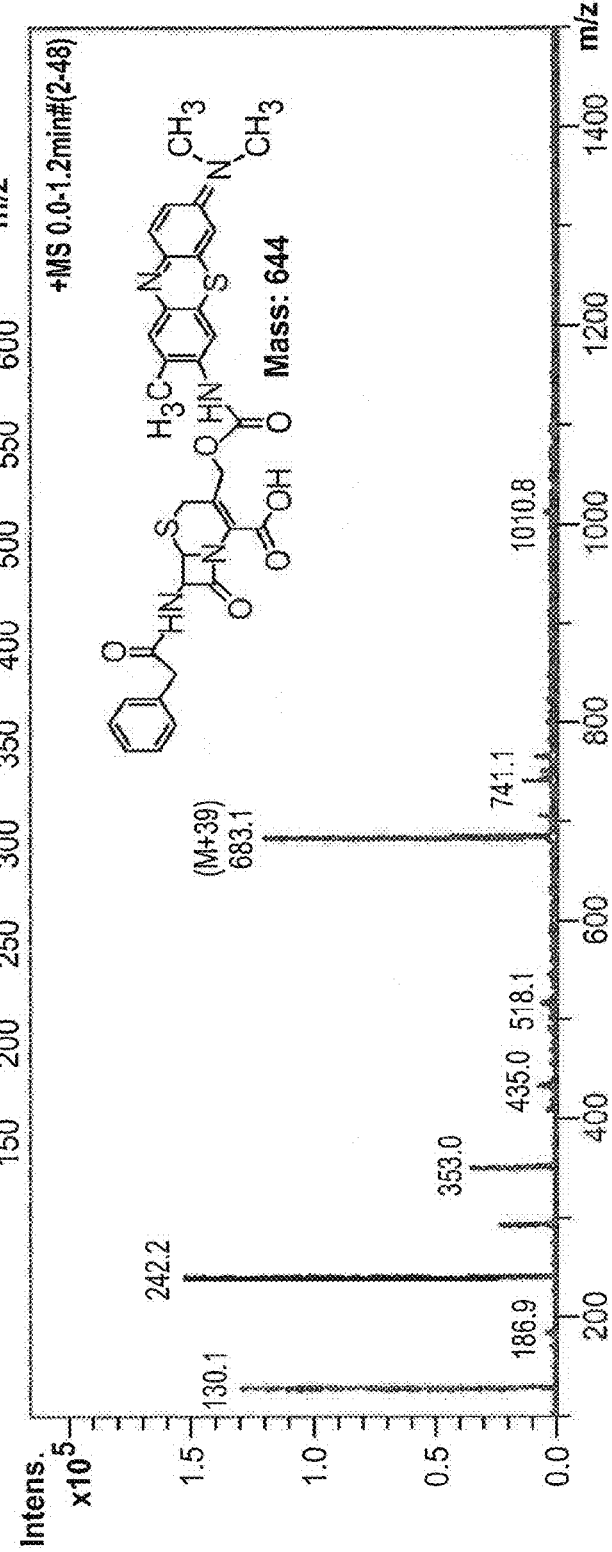

$^1$H NMR spectra were obtained for 7-[(2-phenylacetyl) amino] cephalosporanic acid in $CDCl_3$ as a solvent, as well as for 7-[(2-phenylacetyl)amino] 3-hydrodxymethy cephalosporanic acid in DMSO-$d_6$ as a solvent (FIG. 2). MS spectra were obtained for 7-[(2-phenylacetyl)amino] 3-hydrodxymethy cephalosporanic acid and cephalosporanic acid-toluidine blue O prodrug (FIG. 3).

Figure 4:
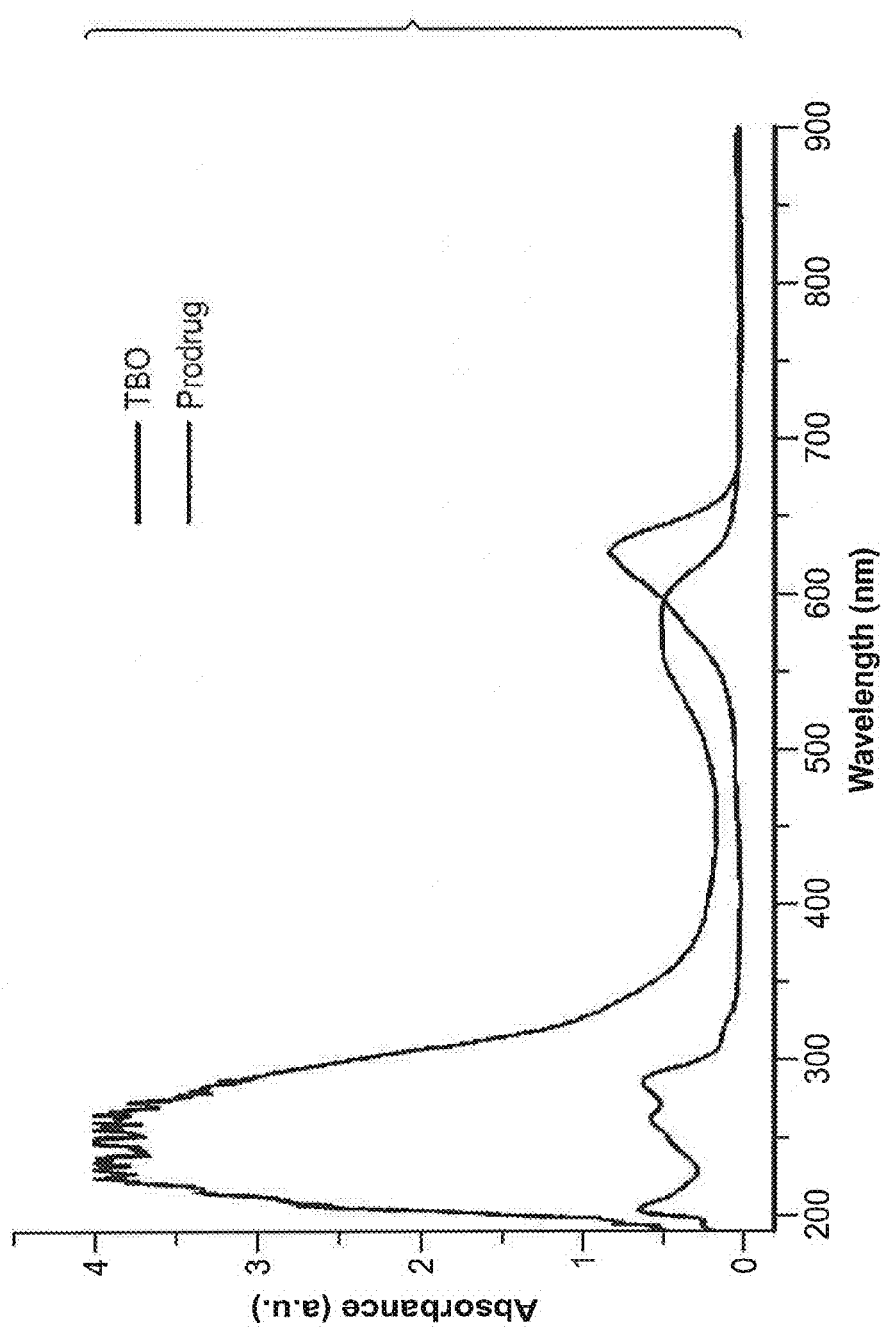
FIG. 4 shows UV-visible spectra obtained for the photosensitizer (TBO) (black line) vs. the Cephalosporanic acid-photosensitizer prodrug (red line) in ethanol at a concentration of $2.0 \times 10^{-5}$ M.
Figure 5:
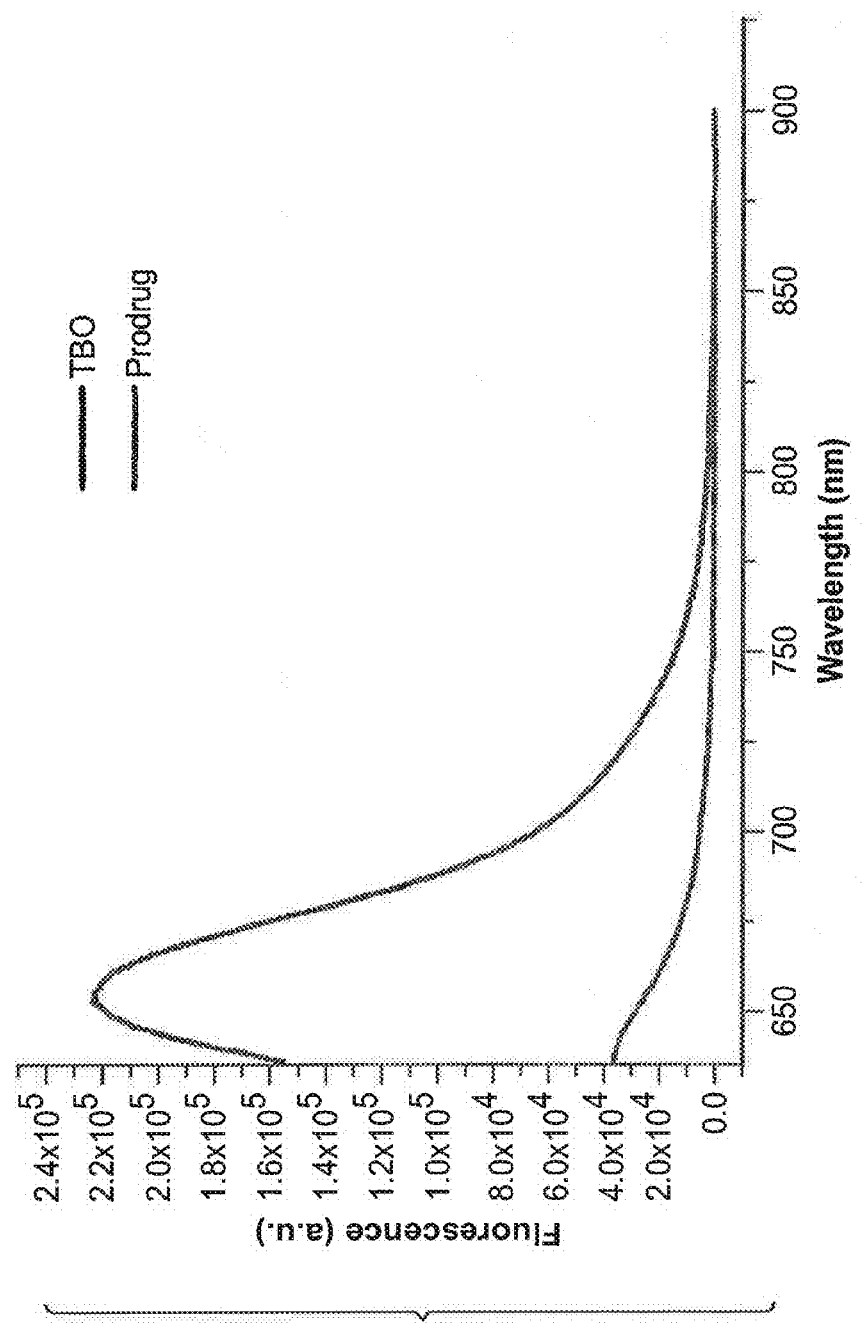
FIG. 5 shows fluorescence emission spectra obtained for the photosensitizer (TBO) (black line) vs. the Cephalosporanic acid-photosensitizer prodrug (red line) in ethanol at 635 nm excitation.

UV-visible spectra revealed blue shift in the absorption spectra of the prodrug, indicating extended conjugation, as well as quenching, of carbamate linked TBO photosensitizer (FIG. 4). Fluorescence spectra revealed nearly an 8-fold reduction in fluorescence emission maxima at 635 nm excitation, indicating quantitative quenching of the photosensitizer upon conjugation with the cephalosporin moiety (FIG. 5).

Enzyme-Mediated Cleavage of the Prodrug

Figure 6A:
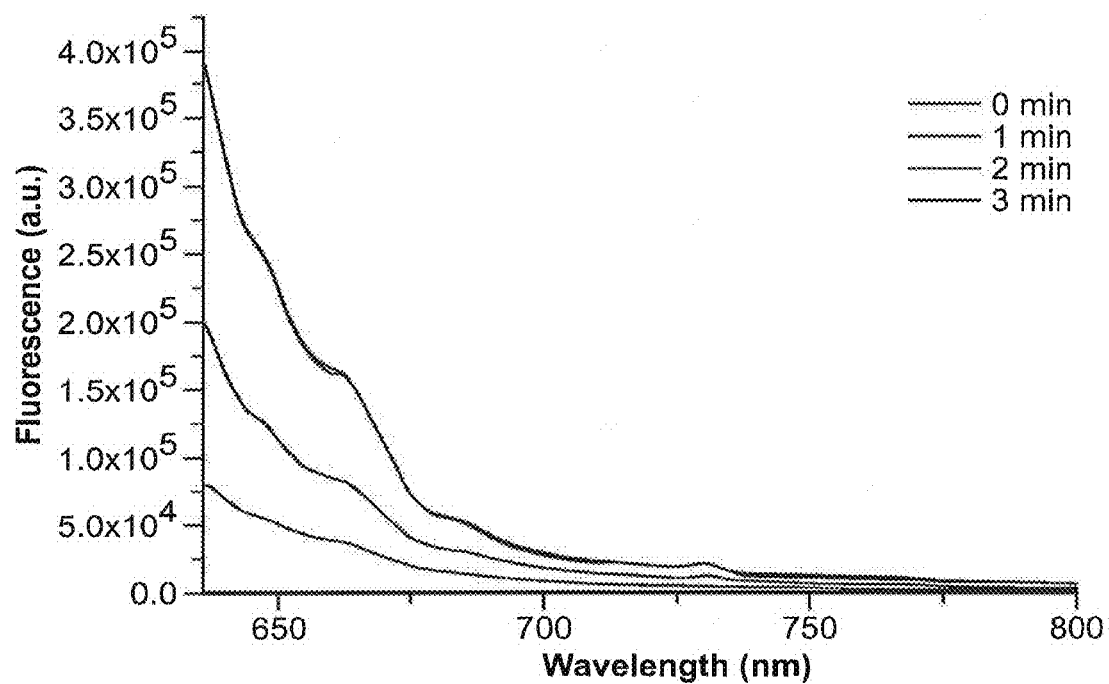
FIGS. 6A and B show plots of (a) fluorescence emission vs. wavelength and (b) fluorescence emission vs. time for the Cephalosporanic acid-photosensitizer prodrug, depicting the enzyme-mediated cleavage of the prodrug.
Figure 6B:
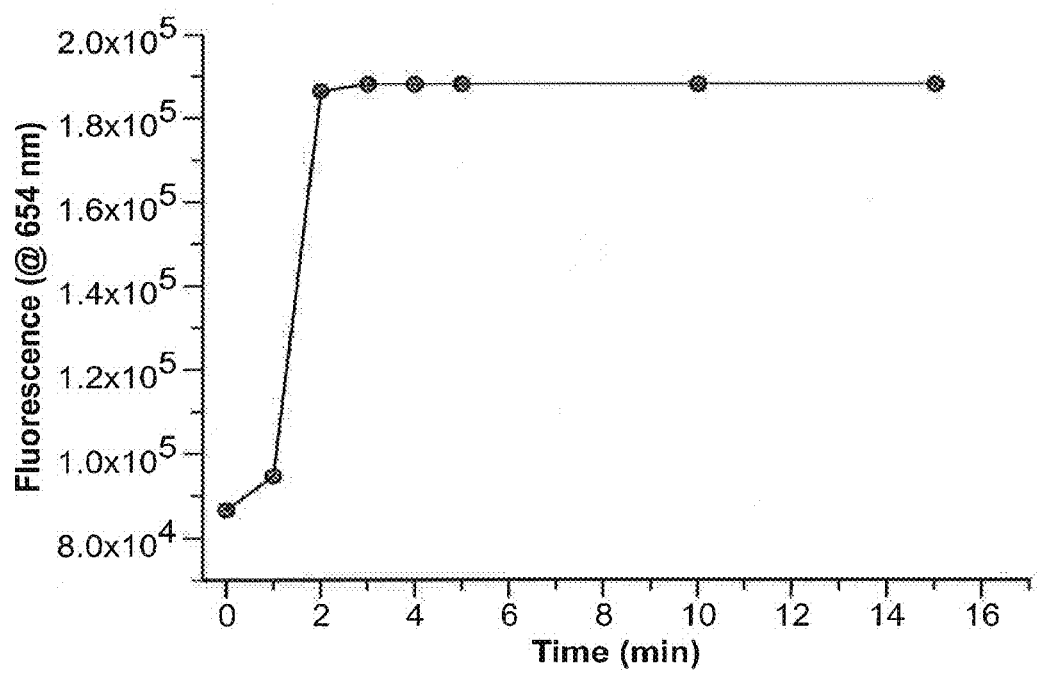

The prodrug obtained was further studied for release of photosensitizer in presence of β-lactamase from *Enterobacter cloacae*. For the fluorescence emission study of the prodrug, the solvent employed was water, and the excitation wavelength 635 nm in the presence of beta-lactamase enzyme (from *Enterobacter cloacae*). Time-dependent fluorescence emission was also measured for photosensitizer release from the prodrug in the presence of enzyme. The results indicate an easy release and nearly 5-fold increase in excited stated properties within minutes of incubation of prodrug with enzyme (FIG. 6). Thus, the prodrug was ynthesized and characterized. Furthermore, the prodrug showed quantitative quenching of the photosensitizer in the conjugated form. Additionally, the product demonstrated lactamase-specific activity.

Example 3

Cleavage of Carbamate-Linked Photosensitizer in Microfilarial *B. malayi*

Figure 8:
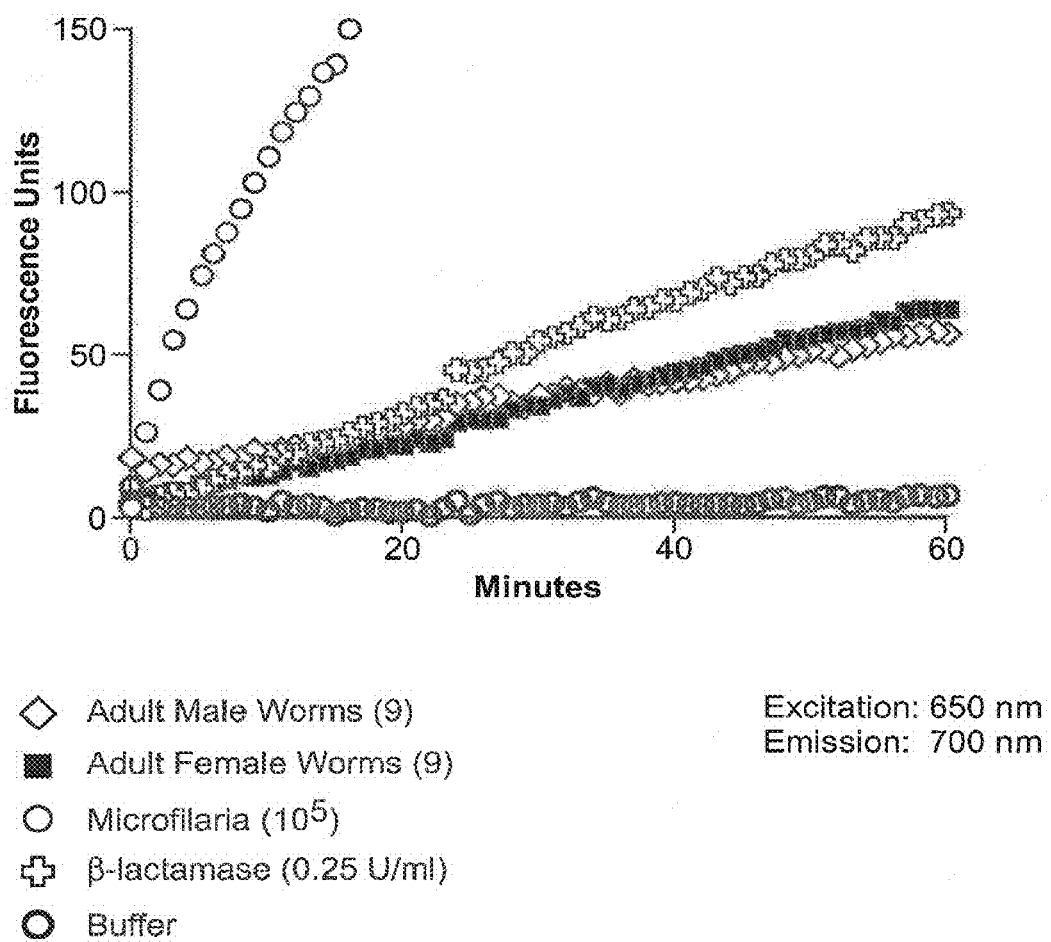
FIG. 8 shows the increasing relative fluorescence resulting from activation of β-LEAP by enzymatic cleavage in *Brugia malayi* adults and 1st stage larvae (microfilariae).

*Brugia malayi* Adults and 1st Stage Larvae (Microfilariae) Activate the β-LEAP Photosensitizer-Containing Construct by Cleavage of the Cephalosporin Moiety. (FIG. 8)

Groups of 3 adult males, 3 adult females and 10,000 microfilariae were incubated with 10 μM β-LEAP in triplicate in the wells of 96 well microtiter plates. Positive control was commercially available *Bacillus cereus* β-lactamase (0.25 U/ml). Negative controls included reactions lacking worms and reactions lacking β-LEAP. Data was collected by a SpectraMax fluorimeter every minute over a 3 hour period with excitation set at 650 nm and emission at 700 nm. Increasing relative fluorescence resulting from activation of β-LEAP by enzymatic cleavage over the first hour of data collection is shown.

Figure 9A:
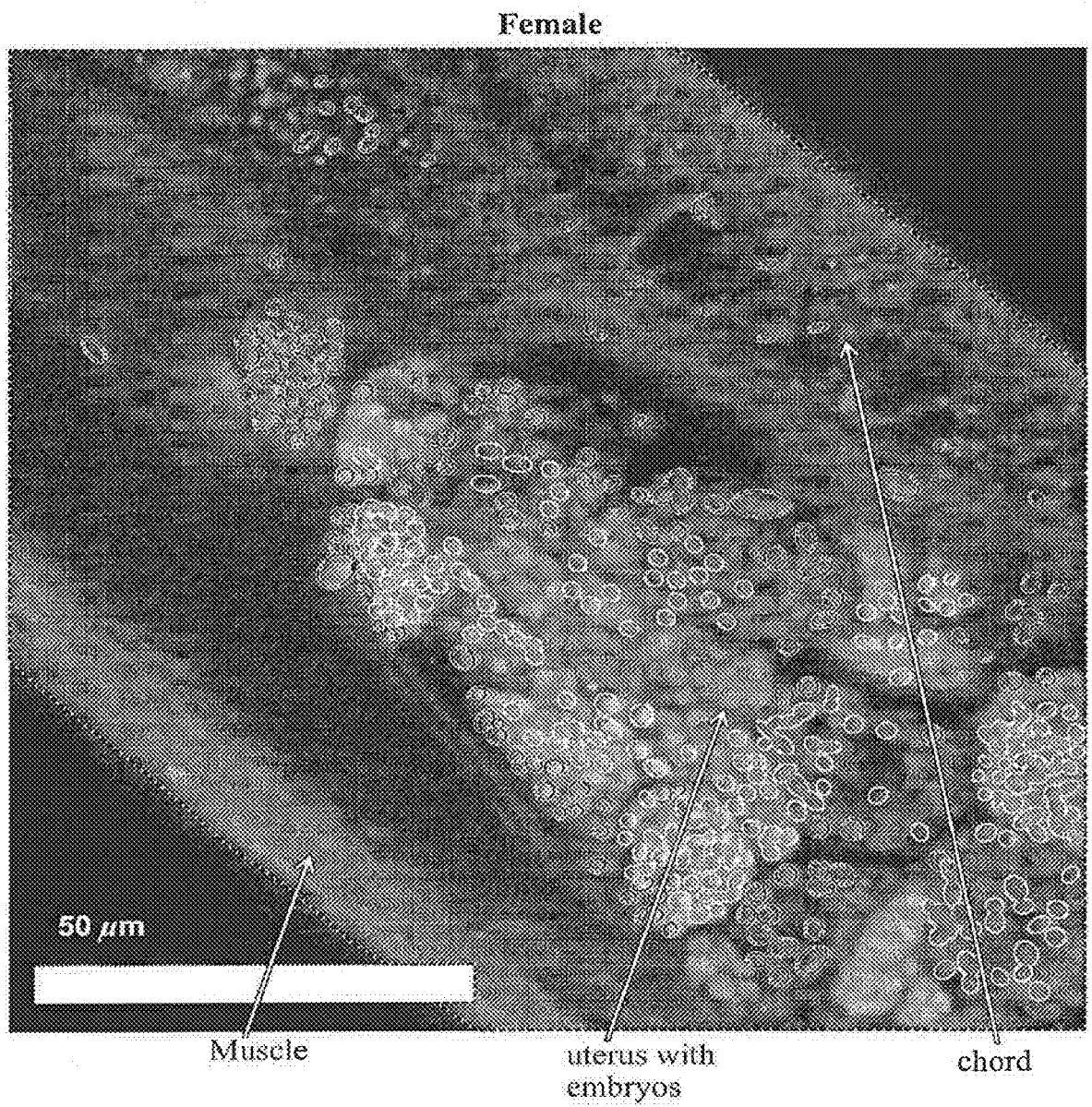
FIGS. 9A-C show a confocal laser scanning micrograph of *Brugia malayi* adults and 1st stage larvae following exposure to β-LEAP and 650 nm light.
Figure 9B:
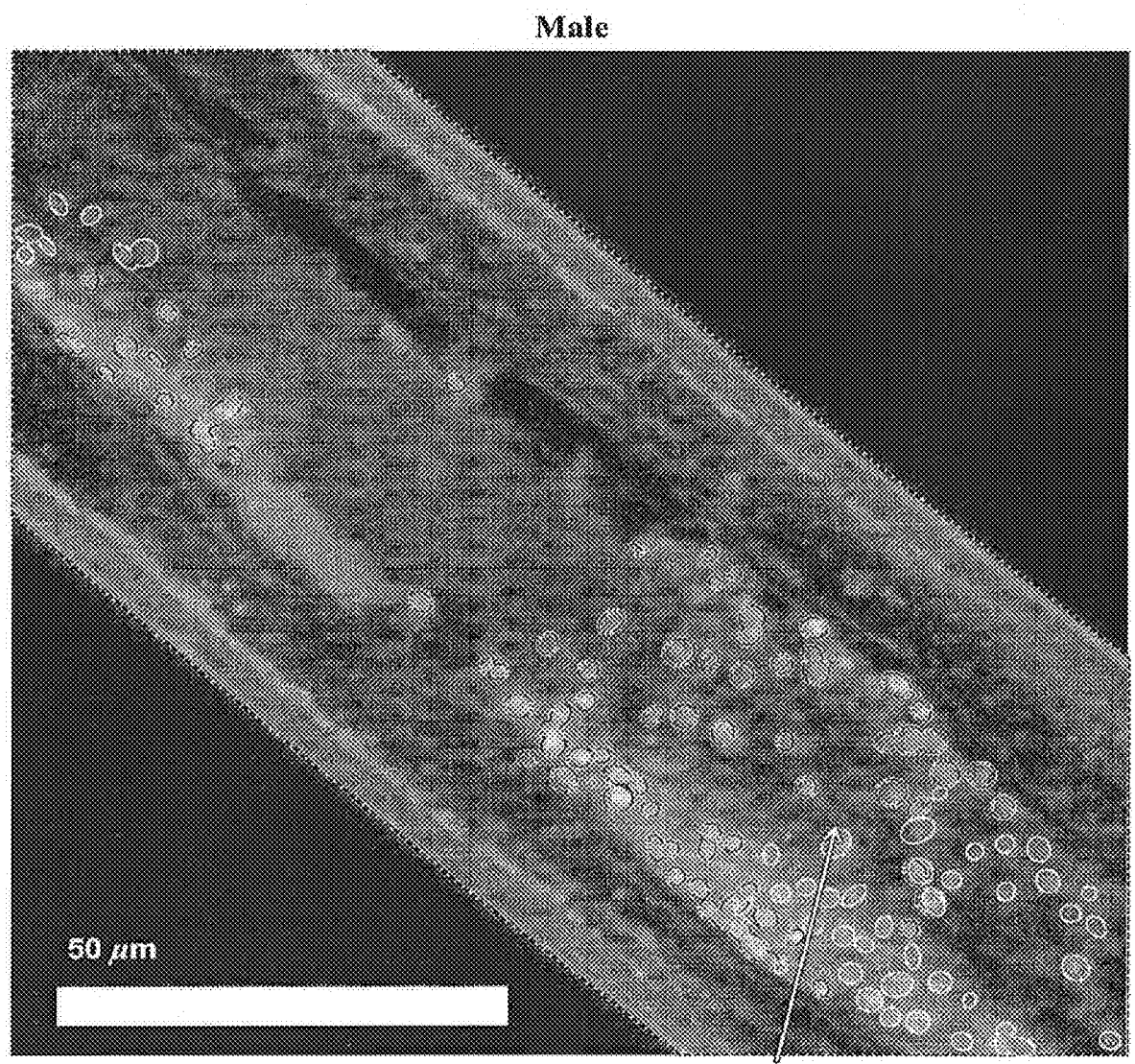
Figure 9C:
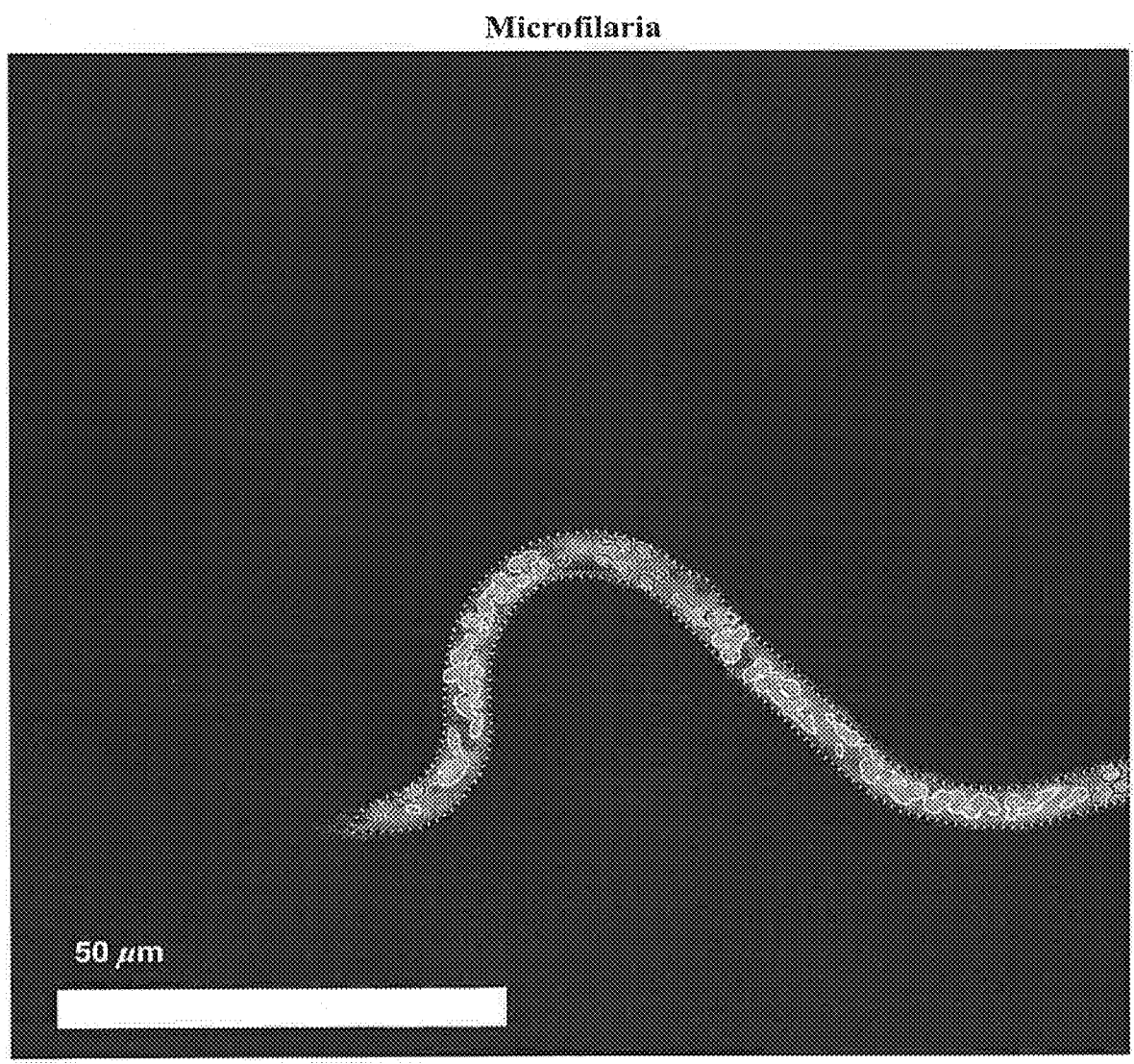

Confocal Laser Scanning Microscopy of *Brugia malayi* Adults and 1$^{st}$ Stage Larvae Following Exposure to β-LEAP and 650 nm Light. (FIG. 9)

Worms recovered from the assay described above were fixed, incubated with RNase and then their nucleic acids stained with propidium iodide. Samples were mounted on glass slides in mounting medium containing DAPI (also stains DNA). Images were acquired using an Olympus FV1000 confocal laser scanning microscope. Images of adult worms are at the region of the reproductive tissue. All images are at 100× magnification and a 50 μm scale bar is provided for reference. The widespread red coloration indicates fluorescence released from β-LEAP, Blue is fluorescence from DAPI and green is fluorescence from propidium iodide.

Figures 10A, 10B:
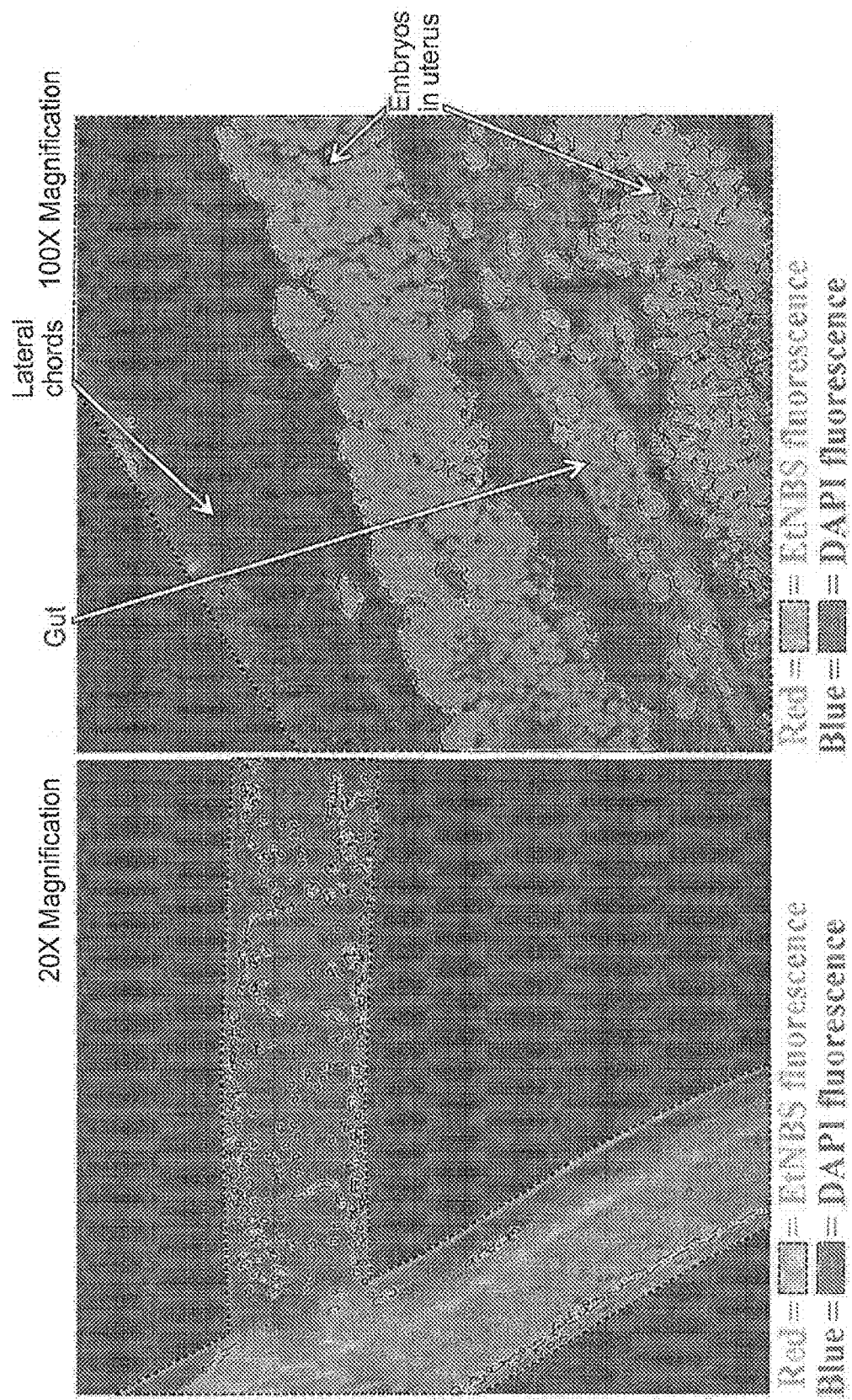
FIGS. 10A-B show a confocal laser scanning microscopy of an adult *Brugia malayi* female following exposure to β-LEAP and 650 nm light.

Confocal Laser Scanning Microscopy of an Adult *Brugia malayi* Female Following Exposure to β-LEAP and 650 nm Light. (FIG. 10)

A female worm recovered from the assay described above was fixed, incubated with RNase and then it's nucleic acids stained with propidium iodide. The worm was mounted on a glass slide in mounting medium containing DAPI (also stains DNA). The images were acquired using an Olympus FV1000 confocal laser scanning microscope. Images are at the region of the reproductive tissue and reveal the intestine. Panel A 20× magnification; Panel B 100× magnification. The widespread red coloration indicates fluorescence released from β-LEAP, Blue is fluorescence from DAPI and green is fluorescence from propidium iodide.

Figure 11:
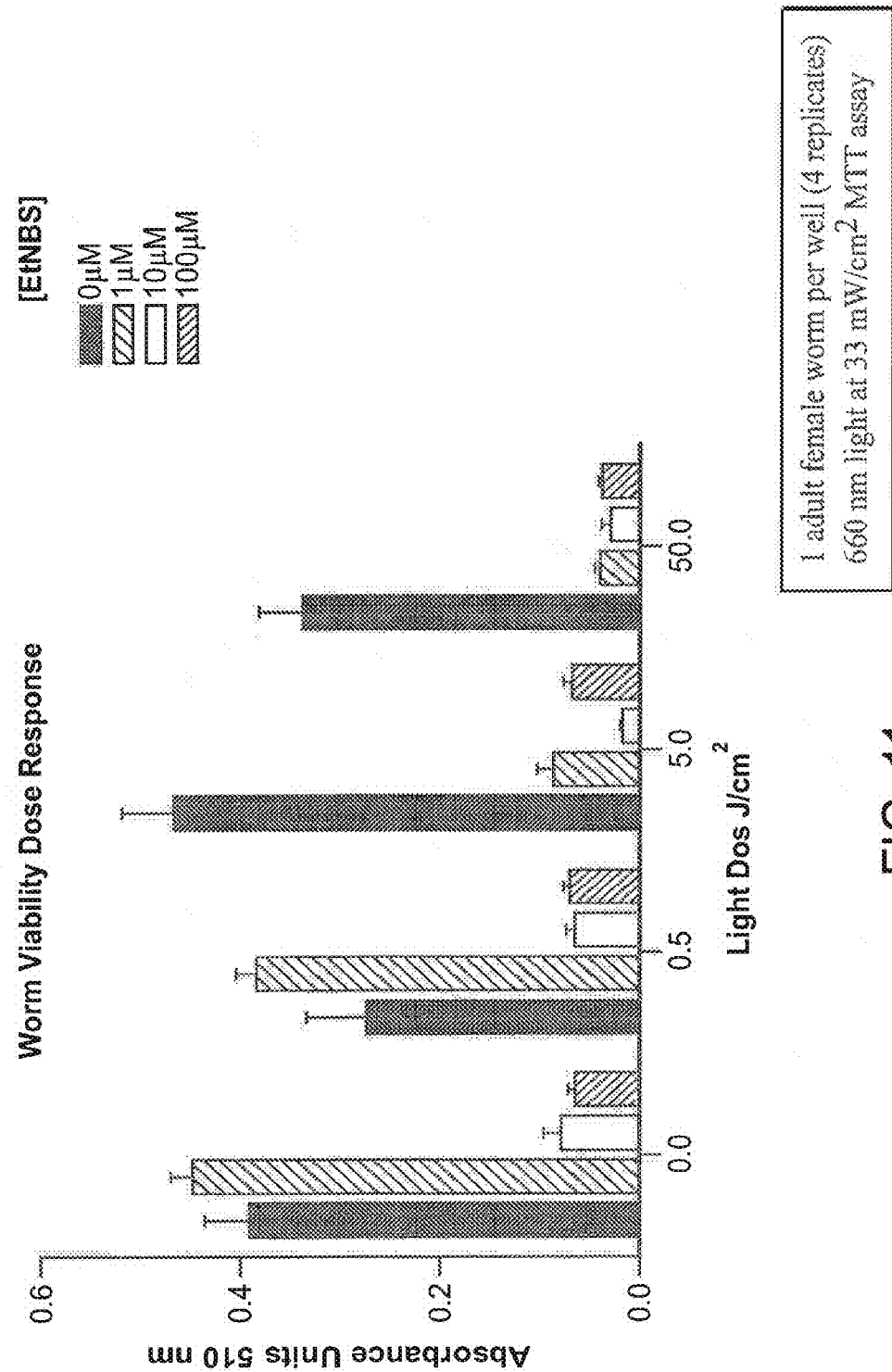
FIG. 11 shows the effects of photodynamic therapy with the photosensitizer EtNBS to kill adult *Brugia malayi*.
Figure 12:
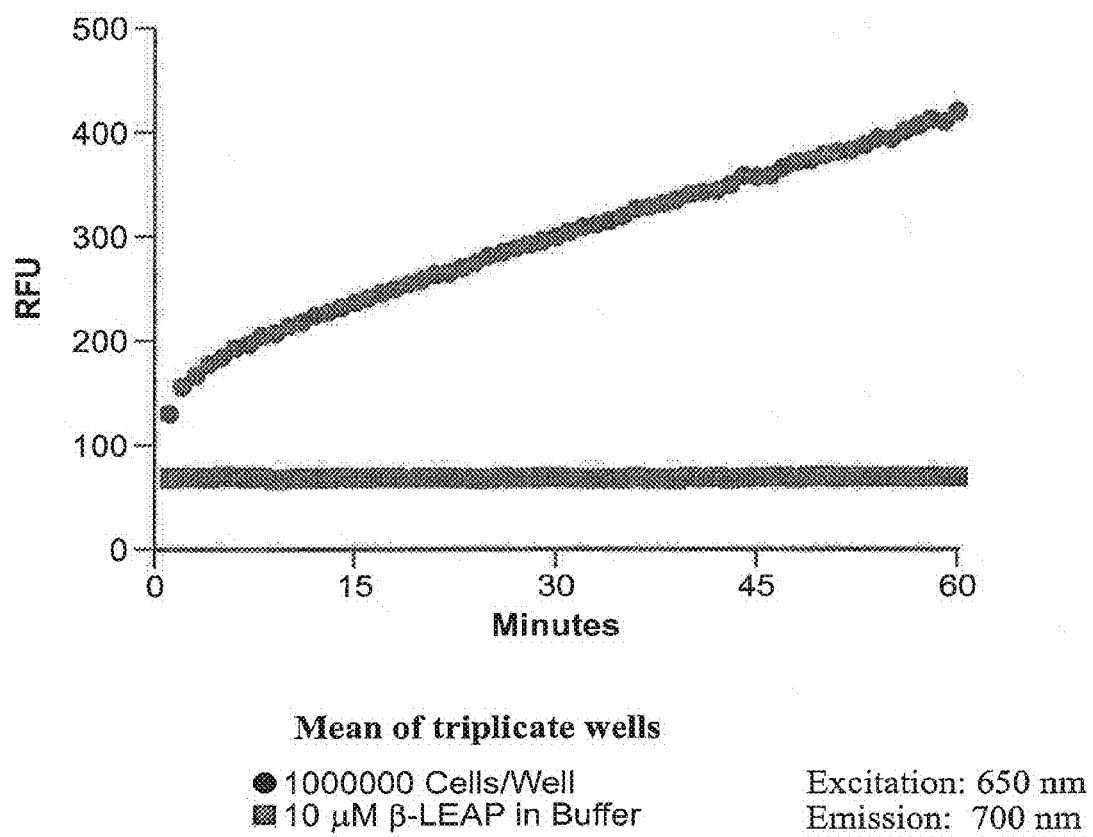
FIG. 12 shows the increasing relative fluorescence resulting from activation of β-LEAP by enzymatic cleavage in *Aedes albopictus* cells.

Photodynamic Therapy with the Photosensitizer EtNBS Kills Adult *Brugia malayi*. (FIG. 11)

Adult female worms were incubated in 10-fold serial dilutions of EtNBS (the photosensitizer that is released from β-LEAP upon enzymatic cleavage) for 16 hr at 37° C. Worms were pooled into groups of 4 and irradiated with light (600 nm at 33 mW/cm$^2$) for different time periods so as to deliver different light doses. Irradiated worms were then returned to standard culture conditions for 24 hrs and the viability of the 4 individual worms from each condition was assessed by use of the MTT assay. The viability of worms from each group is expressed as absorbance units (510 nm) and standard errors are presented. A dose dependent decrease in viability of worms exposed to 1 μM EtNBS is apparent as light dose increases.

Example 4

Cleavage of Carbamate-Linked Photosensitizer in *Aedes albopictus*

*Aedes albopictus* Cells Activate the β-LEAP Photosensitizer-Containing Construct by Cleavage of the Cephalosporin Moiety. (FIG. 11)

The *Aedes albopictus* cell line C6/36 was grown to high density in tissue culture flasks and then 1,000,000 cells were transferred to each of 3 wells of a 96 well microtiter plate and incubated with 10 μM β-LEAP. Positive control was commercially available *Bacillus cereus* β-lactamase (0.25 U/ml). Negative controls included reactions lacking cells and reactions lacking β-LEAP. Data was collected by a SpectraMax fluorimeter every minute over a 3 hour period with excitation set at 650 nm and emission at 700 nm. Increasing relative fluorescence units (RFU) resulting from activation of β-LEAP by enzymatic cleavage over the first hour of data collection is shown.

Example 5

Use of β-LEAP in Industrial Crops Enzymatic Cleavage

Exemplary Formulations:
Pellet Formulation 75 parts by mass of sawdust is impregnated with 20 parts by mass of β-LEAP and 5 parts by mass of cornstarch is added thereto and the mixture is molded into bars to obtain a pellet formulation (cylindrical form 5 to 10 mm long having a diameter of about 2 mm).

Flowable (Emulsion) Formulation 5 parts by mass of polyvinyl alcohol, 3 parts by mass of DEMOL N (trade name; manufactured by Kao Corporation), 0.5 parts by mass of ANTIFOAM E-20 (trade name; manufactured by Kao Corporation) and 41.5 parts by mass of water are stirred and mixed. 50 parts by mass of β-LEAP is added thereto by dropwise to obtain a flowable (emulsion) formulation.

Field Trials:

Field trials are run in accordance with pertinent protocols and in conformance with USDA notification requirements.

Field soil is packed in 350 cm$^2$ plastic pots and seedlings of corn, wheat, sorghum, soybean, and tobacco are sown and covered with soil of about 1 cm thickness. After water absorption and at 11 days after seeding, β-LEAP pellets are spread or a β-LEAP flowable formulation is diluted with a stock solution or water were sprayed uniformly in a spray volume of 200 ml per m$^2$. The test is performed in a glass greenhouse box at a temperature of from 18 to 30° C., and the soil is appropriately moistened from the bottom side.

Pests common to each type of plant are introduced into the respective greenhouse box and allowed to ingest the β-LEAP. After 1 hour, the greenhouse boxes are exposed to sunlight or red LED lighting.

The elimination of the pests is observed.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for controlling an insect pest, the method comprising contacting the pest with an effective amount of a pesticidal composition comprising a compound comprising two or more inactive benzophenothiazinium photosensitizers linked by a cephalosporin linker that is capable of maintaining the photosensitizers in an inactive state, wherein the photosensitizers become photoactivatable when released from the compound upon cleavage by beta-lactamase enzymes present in the pest, wherein exposing the pest to light photoactivates the photosensitizers and generates a phototoxic species sufficient to kill or inhibit the insect pest.

2. The method of claim 1, wherein the benzophenothiazinium photosensitizer is benzophenothiazinium chloride (EtNBS).

3. The method of claim 1, wherein the benzophenothiazinium photosensitizers are each attached to the cephalosporin linker via an ester or carbamate group.

4. The method of claim 1, wherein the insect pest is a mosquito.

5. The method of claim 4, wherein the mosquito is *Aedes* spp., *Anopheles* spp., or *Culex* spp.

6. The method of claim 5, wherein the mosquito is *Aedes albopictus*.

7. The method of claim 1, wherein the insect pest is a parasitic filarial nematode.

8. The method of claim 1, wherein the parasitic filarial nematode is *Brugia malayi*.

9. The method of claim 1, wherein the pesticidal composition is applied in an aerosol, pressure-free spray product, automatic fogging system, fogger, foam, gel, evaporator tablets, liquid evaporator, gel and membrane evaporator, propeller-driven evaporator, energy-free or passive evaporation system, moth paper, as granules or dust, or in baits for spreading or in bait station.

10. The method of claim 1, wherein the pesticidal composition is applied to water.

11. The method of claim 1, further comprising exposing the pest to light to photoactivate the benzophenothiazinium photosensitizers.

12. The method of claim 11, comprising exposing the pest to light comprising 650 nm light.

13. The method of claim 1, wherein the compound comprises the formula:

<chemical structure>

* * * * *

UNITED STATES PATENT AND TRADEMARK OFFICE
CERTIFICATE OF CORRECTION

PATENT NO. : 10,874,107 B2
APPLICATION NO. : 16/013333
DATED : December 29, 2020
INVENTOR(S) : Tayyaba Hasan et al.

Page 1 of 1

It is certified that error appears in the above-identified patent and that said Letters Patent is hereby corrected as shown below:

In the Specification

Column 1, Lines 12, insert -- STATEMENT OF FEDERALLY SPONSORED RESEARCH
This invention was made with government support under Grant No. AR007098 awarded by the National Institutes of Health. The government has certain rights in the invention. --

Signed and Sealed this
Ninth Day of April, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 148
<212> TYPE: PRT
<213> ORGANISM: Brugia malayi

<400> SEQUENCE: 1

Ile Leu Thr Glu Lys Arg Lys Ile Leu Val Asp Cys Gly Asp Pro Trp
1               5                   10                  15

Asn Gly Thr Gln Ile Ile Gln Ala Leu Ser Lys Tyr Ser Leu Asn Cys
            20                  25                  30

Asp Asp Ile Thr Asp Leu Ile Ile Thr His Gly His Ser Asp His Cys
        35                  40                  45
```

```
Gly Asn Leu Ser Leu Phe Gln Gln Ala Lys Ile Tyr Met Gly Asp Asp
     50                  55                  60

Met Ala Lys Asp Gly Ile Tyr Glu Gly Ile Trp Thr Leu Asp Asp Phe
 65              70                  75                      80

Val Lys Ile Arg Pro Thr Pro Gly His Thr Asp Arg Ser Ile Ile Val
                 85                  90                  95

Leu Asp Thr Glu Tyr Gly Thr Val Ala Ile Val Gly Asp Ile Phe Glu
            100                 105                 110

Glu Glu Asn Asp Asp Asp Ser Trp Lys Glu Asn Ser Lys Tyr Pro Glu
        115                 120                 125

Glu Gln Gln Lys Ser Arg Lys Ile Ile Leu Lys Glu Ala Asp Trp Ile
        130                 135                 140

Ile Pro Gly His
145

<210> SEQ ID NO 2
<211> LENGTH: 166
<212> TYPE: PRT
<213> ORGANISM: Aedes aegypti

<400> SEQUENCE: 2

Thr Asn Thr Tyr Ile Ile Gly Thr Gly Lys Arg Arg Ile Leu Leu Asp
 1               5                  10                  15

Ala Gly Asp Glu Asn Val Pro Glu Tyr Ile Gly His Leu Lys Lys Val
             20                  25                  30

Ile Ser Asp Glu Arg Ile Leu Ile Asn Asp Ile Ile Val Ser His Trp
         35                  40                  45

His His Asp His Ile Gly Gly Val Asp Glu Val Leu Asp Ile Ile Glu
     50                  55                  60

Asn Lys Asp Ser Cys Lys Val Trp Lys Phe Pro Arg Ala Asp Ala Pro
 65              70                  75                      80

Asp Gly Thr Ile Arg Asn Ala Asn Ile Asn His Leu Lys His Gly Gln
                 85                  90                  95

Lys Phe Asn Ile Glu Gly Ala Thr Leu Glu Val Leu His Thr Pro Gly
            100                 105                 110

His Thr Thr Asp His Val Val Leu Val Leu His Glu Asp Asn Ser Leu
        115                 120                 125

Phe Ser Ala Asp Cys Ile Leu Gly Glu Gly Ser Thr Val Phe Glu Asp
        130                 135                 140

Leu Tyr Glu Tyr Thr Lys Ser Leu Gln Ala Ile Gln Asp Ala Lys Pro
145                 150                 155                 160

Ser Val Ile Tyr Pro Gly
                165
```